United States Patent
Nagashima et al.

(10) Patent No.: US 12,296,325 B2
(45) Date of Patent: May 13, 2025

(54) CATALYST FOR HYDROSILYLATION REACTION, HYDROGENATION REACTION, AND HYDROSILANE REDUCTION REACTION

(71) Applicants: KYUSHU UNIVERSITY, NATIONAL UNIVERSITY CORPORATION, Fukuoka (JP); SHIN-ETSU CHEMICAL CO., LTD., Tokyo (JP)

(72) Inventors: Hideo Nagashima, Fukuoka (JP); Atsushi Sanagawa, Fukuoka (JP); Shoma Kawabata, Fukuoka (JP); Daisuke Noda, Annaka (JP); Koji Sakuta, Annaka (JP)

(73) Assignees: KYUSHU UNIVERSITY, NATIONAL UNIVERSITY CORPORATION, Fukuoka (JP); SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 18/299,486

(22) Filed: Apr. 12, 2023

(65) Prior Publication Data

US 2023/0241594 A1 Aug. 3, 2023

Related U.S. Application Data

(62) Division of application No. 17/889,003, filed on Aug. 16, 2022, now abandoned, which is a division of application No. 16/489,254, filed as application No. PCT/JP2018/007204 on Feb. 27, 2018, now abandoned.

(30) Foreign Application Priority Data

Feb. 28, 2017 (JP) .................. 2017-036946

(51) Int. Cl.
C07F 7/08 (2006.01)
B01J 31/22 (2006.01)
C07F 7/10 (2006.01)
C07B 47/00 (2006.01)

(52) U.S. Cl.
CPC ......... *B01J 31/2282* (2013.01); *C07F 7/0829* (2013.01); *C07F 7/10* (2013.01); *B01J 2231/323* (2013.01); *B01J 2531/842* (2013.01); *B01J 2531/845* (2013.01); *B01J 2531/847* (2013.01); *C07B 47/00* (2013.01)

(58) Field of Classification Search
None
See application file for complete search history.

(56) References Cited

U.S. PATENT DOCUMENTS

| | | |
|---|---|---|
| 4,332,654 A | 6/1982 | Yates |
| 4,992,573 A | 2/1991 | Lewis |
| 5,389,404 A | 2/1995 | Armstrong |
| 5,523,436 A | 6/1996 | Dauth et al. |
| 5,561,231 A | 10/1996 | Dauth et al. |
| 6,124,418 A | 9/2000 | Crivello et al. |
| 6,303,728 B1 | 10/2001 | Hagimori et al. |
| 6,492,525 B1 | 12/2002 | Bertrand et al. |
| 6,803,440 B2 | 10/2004 | Marko et al. |
| 7,563,741 B2 | 7/2009 | Brummer et al. |
| 8,236,915 B2 | 8/2012 | Delis et al. |
| 8,415,443 B2 | 4/2013 | Delis et al. |
| 8,895,770 B2 | 11/2014 | Lewis et al. |
| 9,073,950 B2 | 7/2015 | Kownacka et al. |
| 9,480,977 B2 | 11/2016 | Brandstadt et al. |
| 2014/0249311 A1 | 9/2014 | Brandstadt et al. |
| 2017/0233417 A1 | 8/2017 | Nagashima et al. |
| 2017/0260216 A1 | 9/2017 | Nagashima et al. |

FOREIGN PATENT DOCUMENTS

| | | |
|---|---|---|
| JP | 1-315344 A | 12/1989 |
| JP | 6-136126 A | 5/1994 |
| JP | 6-263780 A | 9/1994 |

(Continued)

OTHER PUBLICATIONS

Noda et al. Jacs, 2016, 138, 2480-2483 (Year: 2016).*
Bassett et al. J. C. S. Chem. Comm., 1977, 853 (Year: 1977).*
Otsuka et al. Chemical Communications, 1967, 836 (Year: 1967).*
Albers et al., "Catalysed and Non-catalysed Reaction Between [Fe(CO)$_5$] and Isonitriles", J. Chem. Soc., Dalton Trans., 1982, pp. 1069-1079.
Barker et al. J. C. S. Chem. Comm., 256 (Year: 1977).

(Continued)

*Primary Examiner* — Yun Qian

(74) *Attorney, Agent, or Firm* — Birch, Stewart, Kolasch & Birch, LLP

(57) ABSTRACT

Provided is a catalyst which comprises a compound represented by formula (1) and which exhibits activity for at least one type of reaction selected from among hydrosilylation reaction or hydrogenation reaction with respect to an aliphatic unsaturated bond and hydrosilane reduction reaction with respect to a carbon-oxygen unsaturated bond or a carbon-nitrogen unsaturated bond. Formula (1): $M_n(L_m)$ {M represents Fe, Co, or Ni having an oxidation number of 0, L represents an isocyanide ligand represented by formula (2), n denotes an integer of 1-8, and m denotes an integer of 2-12. Formula (2): $(CN)_x$—$R^1$ ($R^1$ represents a mono- to trivalent-organic group having 1-30 carbon atoms, optionally being substituted by a halogen atom, and optionally having interposed therein one or more atoms selected from among O, N, S, and Si; and x denotes an integer of 1-3)}.

2 Claims, No Drawings

(56) References Cited

FOREIGN PATENT DOCUMENTS

| JP | 7-149780 | A | 6/1995 | | |
|---|---|---|---|---|---|
| JP | 11-228579 | A | 8/1999 | | |
| JP | 2001-131231 | A | 5/2001 | | |
| JP | 3174616 | B2 | 6/2001 | | |
| JP | 3599669 | B2 | 12/2004 | | |
| JP | 3854151 | B2 | 12/2006 | | |
| JP | 4007467 | B2 | 11/2007 | | |
| JP | 4249702 | B2 | 4/2009 | | |
| JP | 2012-532884 | A | 12/2012 | | |
| JP | 2012-532885 | A | 12/2012 | | |
| JP | 2013-544824 | A | 12/2013 | | |
| JP | 2014-502271 | A | 1/2014 | | |
| JP | 2014-503507 | A | 2/2014 | | |
| WO | WO2010/016416 | A1 | 2/2010 | | |
| WO | WO 2013/043783 | A2 | 3/2013 | | |
| WO | WO 2013/043785 | A2 | 3/2013 | | |
| WO | WO 2013/043787 | A2 | 3/2013 | | |
| WO | WO 2013/043846 | A1 | 3/2013 | | |
| WO | WO 2013/043912 | A2 | 3/2013 | | |
| WO | WO 2013/081794 | A1 | 6/2013 | | |
| WO | WO 2014/021908 | A1 | 2/2014 | | |
| WO | WO-2016024607 | A1 * | 2/2016 | .......... | B01J 31/1805 |
| WO | WO-2016027819 | A1 * | 2/2016 | .............. | B01J 31/18 |

OTHER PUBLICATIONS

Barker et al., "Synthesis and Reactions of Octakis(t-butyl isocyanide)dicobalt and Pentakis(t-butylisocyanide)ruthenium; X-Ray Crystal and Molecular Structures of [Co$_2$(Bu$^t$NC)$_8$] and [Ru(Ph$_3$P)(Bu$^t$(NC)$_4$]", J.C.S. Chem. Comm., 1977, pp. 256-258.

Bart et al., "Preparation and Molecular and Electronic Structures of Iron(0) Dinitrogen and Silane Complexes and Their Application to Catalytic Hydrogenation and Hydrosilation", Journal of American Chemical Society, vol. 126, No. 42, Oct. 5, 2004, pp. 13794-13807.

Bassett et al., "Chemistry of Low-valent Metal Isocyanide Complexes. Part 1. Synthesis of Zerovalent Iron and Ruthenium Complexes. Crystal and Molecular Structures of Tetrakis (t-butyl isocyanide) (triphenylphosphine) ruthenium and Pentakis (t-butyl isocyanide) iron", J. Chem. Soc., Dalton Trans., 1979 pp. 1003-1011.

Bassett et al., "Chemistry of Low-valent Metal Isocyanide Complexes. Part 3. The Synthesis, Structure, and Dynamic Behaviour of Nonakis(ethyl and isopropyl isocyanide)di-iron and -ruthenium Complexes. Crystal Structure of [Fe$_2$ (μ-CNEt)$_2$(CNEt)$_6$]", J. Chem. Soc., Dalton Trans., 1981, pp. 219-227.

Brookhart et al., "Mechanism of a Cobalt (III)-Catalyzed Olefin Hydrosilation Reaction: Direct Evidence for a Silyl Migration Pathway", J. Am. Chem. Soc., vol. 115, No. 6, 1993, pp. 2151-2156.

Brown, "Reductions by Lithium Aluminum Hydride", Organic Reactions, Chapter 10, vol. 6, 1941, pp. 469-493.

Carroll et al., "Synthesis, Molecular Structure, and Dynamic Behaviour in Solution of Octakis(t-butylisocyanide)dicobalt", J. Chem. Soc., Dalton Trans., 1980, pp. 80-86.

Chalk et al., "Homogeneous Catalysis. IV. Some Reactions of Silicon Hydrides in the Presence of Cobalt Carbonyls", J. Am. Chem. Soc., vol. 89, No. 7, Mar. 29, 1967, pp. 1640-1647.

Chalk, "The Hydrosilation of Olefins Catalyzed by Some Rhodium and Cobalt Complexes", J. Organomet. Chem., vol. 21, 1970, pp. 207-213.

Chatani et al., "The Co$_2$(CO)$_8$-Catalyzed Hydrosilylation of Oxygen-Containing Olefins: Silylmetalation as a Key Step", Chemistry Letters, 2000, pp. 14-15.

Chen et al., "Iron-Catalyzed Asymmetric Hydrosilylation of 1,1-Disubstituted Alkenes", Angew. Chem. Int. Ed., vol. 54, 2015, pp. 4661-4664.

Chen et al., "Rapid, Regioconvergent, Solvent-Free Alkene Hydrosilylation with a Cobalt Catalyst", J. Am. Chem. Soc., vol. 137, Oct. 7, 2015, pp. 13244-13247.

Daida et al., "Considering Fe II/IV Redox Processes as Mechanistically Relevant to the Catalytic Hydrogenation of Olefins by [PhBP/Pr$_3$]Fe-H$_x$ Species", Inorg. Chem., vol. 43, No. 23, 2004, pp. 7474-7485.

Das et al., "Two iron Catalysts are Better than One: A General and Convenient Reduction of Aromatic and Aliphatic Primary Amides", Angew. Chem. Int. Ed., vol. 51, 2012, pp. 1662-1666.

Dombray et al., "Cobalt Carbonyl-Based Catalyst for Hydrosilylation of Carboxamides", Adv. Synth. Catal., vol. 355, Nov. 4, 2013, pp. 3358-3362.

Extended European Search Report issued Jan. 13, 2021, in European Patent Application No. 18760250.3.

Frankel et al., "Homogeneous Hydrogenation of Methyl Linoleate Catalyzed by Iron Pentacarbonyl. Characterization of Methyl Octadecadienoate-Iron Tricarbonyl Complexes", J. Org. Chem., vol. 29, Nov. 1964, pp. 3292-3297.

Gieshoff et al., "Iron-Catalyzed Olefin Hydrogenation at 1 Bar H$_2$ with a FeCl$_3$—LiAlH$_4$Catalyst", Green Chem., vol. 17, 2015, pp. 1408-1413.

Guo et al., "Cobalt-catalyzed Asymmetric Hydroboration of Aryl Ketones with Pinacolborane", Chem. Commun., vol. 51, 2015, pp. 5725-5727.

Harmon et al., "Hydrogenation of Organic Compounds Using Homogeneous Catalysts", J. Chem, Rev., vol. 73, No. 1, 1973, pp. 21-52.

Harrod et al., "Dicobalt Octacarbonyl as a Catalyst for Hydrosilation of Olefins", Communications to the Editor, 1965, p. 1133.

Hyder et al., "Oligomerization and Regioselective Hydrosilylation of Styrenes Catalyzed by Cationic Allyl Nickel Complexes Bearing Allylphosphine Ligands", Dalton Trans., Jun. 18, 2007, pp. 3000-3009.

Inagaki et al., "Asymmetric Iron-Catalyzed Hydrosilane Reduction of Ketones: Effect of Zinc Metal upon the Absolute Configuration", Angew. Chem. Int. Ed., vol. 49, 2010, pp. 9384-9387.

Inagaki et al., "Iron- and Cobalt-Catalyzed Asymmetric Hydrosilylation of Ketones and Enones with Bis(oxazolinylphenyl)amine Ligands", Chem. Eur. J., vol. 16, Jan. 29, 2010, pp. 3090-3096.

International Search Report and the Written Opinion of the International Searching Authority for International Application No. PCT/JP2018/007204, dated Apr. 10, 2018.

Jones et al., "Preparation and Structural Examination of a Series of New, Low-Valent Iron Phosphine Isocyanide Complexes with Bent C-N-C Linkages", Inorg. Chem., vol. 26, No. 13, 1987, pp. 2120-2127.

Junquera et al., "R-Allyl Nickel (II) Complexes with Chelating N-Heterocyclic Carbenes: Synthesis, Structural Characterization, and Catalytic Activity", Organometallics, vol. 31, Mar. 5, 2012, pp. 2175-2183.

Kakiuchi et al., "Completely Selective Synthesis of (E)-β-(Triethylsilyl) Styrenes by Fe$_3$(CO)$_{12}$-Catalyzed Reaction of Styrenes with Triethylsilane", Journal of Organometallic Chemistry, vol. 456, 1993, pp. 45-47.

Kamata et al., "Catalytic Hydrosilylation of Alkenes by Iron Complexes Containing Terpyridine Derivatives as Ancillary Ligands", Organometallics, vol. 31, May 8, 2012, pp. 3825-3828.

Kiso et al., "Silicon Hydrides and Nickel Complexes", J. Organomet. Chem., vol. 50, 1973, pp. 297-310.

Leach et al., "Synthesis and Structural Characterization of [Co(CN(2,6-C$_6$H$_3$Me$_2$)}$_4$], the First Transition Metal Isonitrilate", J. Am. Chem. Soc., vol. 116, No. 19, 1994, pp. 8566-8574.

Lentz et al., "Transition Metal Complexes and Cycloaddition Products of Pentafluorophenyl Isocyanide", J. Fluorine Chem., vol. 89, 1998, pp. 73-81.

Lentz, "Homoleptische Trifluormethylisocyanid-Eisenkomplexe, Fe(CNCF$_3$)$_5$ und Fe$_2$(CNCF$_3$)$_9$,", J. Organomet. Chem., vol. 377, 1989, pp. 305-308, with English Abstract.

Lin et al., "Boryl-Mediated Reversible H$_2$ Activation at Cobalt: Catalytic Hydrogenation, Dehydrogenation, and Transfer Hydrogenation", J. Am. Chem. Soc., vol. 135, Sep. 30, 2013, pp. 15310-15313.

Lipschutz et al., "Sythesis and Reactivity of a Conveniently Prepared Two-Coordinate Bis(amido) Nickel(II) Complex", Chem. Commun., vol. 48, Jun. 12, 2012, 7146-7148.

Maciejewski et al., "Catalysis of Hydrosilylation| Part XXXIV. High Catalytic Efficiency of the Nickel Equivalent of Karstedt Catalyst", J. Organomet. Chem., vol. 597, 2000, pp. 175-181.

Magomedov et al., "Hydrosilylation of Olefins in the Presence of Metal Carbonyls", J. Organomet Chem., vol. 149, 1978, pp. 29-36.

(56) References Cited

OTHER PUBLICATIONS

Margulieux et al., "Isocyano Analogues of [Co(CO)₄]ⁿ: A Tetraisocyanide of Cobalt Isolated in Three States of Charge", J. Am. Chem. Soc., vol. 132, No. 14, 2010, pp. 5033-5035.

Mo et al., "Anchoring of Silyl Donors on a N-Heterocyclic Carbene Through the Cobalt-Mediated Silylation of Benzylic C-H Bonds", Angew. Chem. Int. Ed., vol. 52, 2013, pp. 10845-10849.

Mokhtarzadeh et al., "Synthesis and Protonation of an Encumbered Iron Tetraisocyanide Dianion", Inorg. Chem., vol. 54, May 12, 2015, pp. 5579-5587.

Muetterties et al., "Metal Clusters. 23. Tetranuclear Nickel Alkyl Isocyanide Clusters", Inorg. Chem., vol. 19, No. 6, 1980, pp. 1552-1560.

Murai et al., "Cobalt Carbonyl Catalyzed Hydrosilylation of Nitriles: A New Preparation of N, N-Disilylamines", J. Org. Chem., vol. 55, No. 2, 1990, pp. 449-453.

Murai et al., "Synthesis and Structure of N-(Silylalkyl)amides: Rhodium-Catalyzed Hydrosilylation of Enamides", Organometallics, vol. 17, No. 5, Feb. 5, 1998, pp. 926-932.

Nakamura et al., "Cylopropanation Reactions of Diazoalkanes with Substituted Olefins in the Presence and Absence of Nickel(0) and Palladium(0) Catalysts. The Structure of (Diazofluorene)bis(tert-butyl isocyanide)nickel(0); a Complex containing a 4-Bonded Diazofluorene Molecule " Journal of the Americal Chemical Society (Mar. 30, 1977) vol. 99 No. 7 pp. 2108-2117.

Naumov et al., "Selective Dehydrogenative Silylation-Hydrogenation Reaction of Divinyldisiloxane with Hydrosilane Catalyzed by an Iron Complex", Journal of the American Chemical Society, vol. 134, 2012 (Dec. 29, 2011), pp. 804-807.

Nesmeyanov et al., "Addition, Substitution, and Telomerization Reactions of Olefins in the Presence of Metal Carbonyls or Colloidal Iron", Tetrahedron, vol. 17, 1962, pp. 61-68.

Noda et al., "Non-Precious-Metal Catalytic Systems Involving Iron or Cobalt Carboxylates and Alkyl Isocyanides for Hydrosilylation of Alkenes with Hydrosiloxanes", J. Am. Chem. Soc., vol. 138, Jan. 13, 2016, pp. 2480-2483, 41 pages total.

Perales et al., "Thioether-Directed Platinum-Catalyzed Hydrosilylation of Olefins", J. Org. Chem., vol. 66, No. 22, 2001, pp. 7270-7274.

Rangheard et al., "At the Frontier Between Heterogeneous and Homogeneous Catalysis: Hydrogenation of Olefins and Alkynes with Soluble Iron Nanoparticles", Dalton Trans., vol. 39, 2010, pp. 8464-8471.

Reichel et al., "Photochemistry of Cobalt Carbonyl Complexes Having a Cobalt-Silicon Bond and Its Importance in Activation of Catalysis" Inorg. Chem., vol. 19, No. 12, 1980, pp. 3858-3860.

Schroeder et al., "Pentacarbonyliron (0) Photocatalyzed Hydrogenation and Isomerization of Olefins", J. Am. Chem. Soc., vol. 98, No. 2, Jan. 21, 1976, pp. 551-558.

Schroeder et al., "Pentacarbonyliron(0) Photocatalyzed Reactions of Trialkylsilanes with Alkenes", Journal of Organometallic Chemistry, vol. 128, 1977, pp. 345-358.

Schuster et al., "Bench-Stable, Substrate-Activated Cobalt Carboxylate Pre-Catalysts for Alkene Hydrosilylation with Tertiary Silanes", ACS Catal., vol. 6, Mar. 18, 2016, pp. 2632-2636.

Sunada et al., "Combinatorial Approach to the Catalytic Hydrosilylation of Styrene Derivatives: Catalyst Systems Composed of Organoiron(0) or (II) Precursors and Isocyanides", Organometallics, vol. 34, Jun. 3, 2015, pp. 2896-2906.

Sunada et al., "Hydrosilane Reduction of Tertiary Carboxamides by Iron Carbonyl Catalysts", Angew. Chem. Int. Ed., vol. 48, 2009, pp. 9511-9514.

Takeshita et al., "The Catalyzed Reaction of α,β-Unsaturated Esters with Various Hydrosilanes", J. Org. Chem., vol. 52, No. 22, 1987, pp. 4864-4868.

Thomas et al., "Metal Clusters in Catalysis. 6. Synthesis and Chemistry of $Ni_4[CNC(CH_3)_3]_7$ and Related Clusters", J. Am. Chem. Soc., vol. 99, No. 3, Feb. 2, 1977, pp. 743-748.

Tokmic et al., "Well-Defined Cobalt (I) Dihydrogen Catalyst: Experimental Evidence for a Co(I)/Co(III) Redox Process in Olefin Hydrogenation", J. Am. Chem. Soc., vol. 138, Aug. 29, 2016, pp. 11907-11913.

Tondreau et al., "Synthesis, Electronic Structure, and Alkene Hydrosilylation Activity of Terpyridine and Bis(imino)pyridine Iron Dialkyl Complexes", Organometallics, vol. 31, Jun. 27, 2012, pp. 4886-4893.

Tondreau et al., "Iron Catalysts for Selective Anti-Markovnikov Alkene Hydrosilylation Using Tertiary Silanes", Science, vol. 335, Feb. 3, 2012, pp. 567-570, 5 pages total.

Tsutsumi et al., "New Catalyst Systems for Iron-Catalyzed Hydrosilane Reduction of Carboxamides", Chem. Commun., vol. 47, May 12, 2011, pp. 6581-6583.

Voronkov et al., "The Catalytic Reactions of Triethyl- and Triethoxy-Silane with Unsaturated Sulphides", J. Organomet. Chem., vol. 190, 1980, pp. 335-341.

Yamamoto et al., "Synthesis and Reactions of Dicobalt Octaisocyanide", Inorg. Chem., vol. 17, No. 11, 1978, pp. 3111-3114.

Yu et al., "High-Activity Iron Catalysts for the Hydrogenation of Hindered, Unfunctionalized Alkenes", ACS Catal., vol. 2, Jul. 23, 2012, pp. 1760-1764.

Zhou et al., "A Convenient and General Iron-Catalyzed Reduction of Amides to Amines", Angew. Chem. Int.Ed., vol. 48, 2009, pp. 9507-9510.

\* cited by examiner

CATALYST FOR HYDROSILYLATION REACTION, HYDROGENATION REACTION, AND HYDROSILANE REDUCTION REACTION

CROSS-REFERENCE TO RELATED APPLICATIONS

This application is a Divisional of U.S. application Ser. No. 17/889,003 filed on Aug. 16, 2022, which is a Divisional of U.S. Ser. No. 16/489,254 filed on Aug. 27, 2019 (abandoned), which is the U.S. National Phase of PCT/JP2018/007204, filed on Feb. 27, 2018, and which claims priority under 35 U.S.C. § 119(a) to Application No. 2017-036946 filed in Japan, on Feb. 28, 2017, the entire contents of all of which are expressly incorporated by reference into the present application.

TECHNICAL FIELD

The present invention relates to a catalyst made of a prescribed metal-isocyanide complex, and relates more specifically to a catalyst having activity in at least one reaction selected from hydrosilylation reaction or hydrogenation reaction on an aliphatic unsaturated bond and hydrosilane reduction reaction on a carbon-oxygen unsaturated bond or a carbon-nitrogen unsaturated bond.

BACKGROUND ART

Hydrosilylation reaction which is addition of a Si—H functional compound to a compound having a carbon-carbon double bond or triple bond is a useful method for the synthesis of organosilicon compounds and an industrially important synthesis reaction.

As the catalyst for hydrosilylation reaction, Pt, Pd and Rh compounds are known. Among others, Pt compounds as typified by Speier's catalyst and Karstedt's catalyst are most commonly used.

While several problems arise with reaction in the presence of Pt compounds as the catalyst, one problem is that upon addition of a Si—H functional compound to terminal olefin, a side reaction due to internal rearrangement of olefin takes place. Since this system does not exert addition reactivity to the internal olefin, unreacted olefin is left in the addition product. To drive the reaction to completion, it is necessary to use an excess amount of olefin in advance by taking into account the left by the side reaction.

Another problem is that the selectivity of α- and β-adducts is low depending on the type of olefin.

The most serious problem is that all the center metals Pt, Pd and Rh are quite expensive noble metal elements. As metal compound catalysts which can be used at lower cost are desired, a number of research works have been made thereon.

For example, reaction in the presence of iron-carbonyl complexes ($Fe(CO)_5$, $Fe_3(CO)_{12}$) is known from Non-Patent Document 1, although this reaction requires reaction conditions including as high a temperature as 160° C. or photo-irradiation (Non-Patent Document 2).

For these iron-carbonyl complexes, it is reported in Non-Patent Document 3 and Patent Document 1 that products formed by dehydrogenative silylation are obtained rather than the addition reaction.

Also, Non-Patent Document 4 and Patent Document 2 report a reaction of methylvinyldisiloxane and methylhydrogendisiloxane in the presence of an iron-carbonyl complex coordinated with a cyclopentadienyl group. Since dehydrogenative silylation reaction takes place along with the relevant reaction, the selectivity of addition reaction is low.

Non-Patent Document 5 refers to reaction in the presence of an iron catalyst having a terpyridine ligand. Although $PhSiH_3$ and $Ph_2SiH_2$ add to olefins, more useful trialkylsilanes, alkoxysilanes and siloxanes have poor addition reactivity to olefins.

Non-Patent Document 6 reports that from reaction in the presence of an iron catalyst having a terpyridine ligand and a bistrimethylsilylmethyl group, an addition reaction product is obtained in high yields. This method needs a catalyst synthesis, including first synthesizing a terpyridine-iron complex as a catalyst precursor and introducing a bistrimethylsilylmethyl group therein at a low temperature, which is not easy.

Also, Non-Patent Documents 7 and 8 report iron complexes having a bisiminopyridine ligand. It is disclosed that they exhibit high reactivity to alkoxysilanes and siloxanes under mild conditions.

However, at the time of the synthesis of this complex, there are points at issue such as using Na amalgam, which consists of water-sensitive sodium and highly toxic mercury and needs care in handling (or using water-sensitive $NaBEt_3H$), and the storage requiring the conditions of being at low temperature in an inert-gas nitrogen atmosphere because of the low stability of the complex compound itself.

Also an iron complex having a chiral iminopyridine oxazoline ligand is reported (Non-Patent Document 9), and the report shows an example of reaction between a tertiary alkene and $Ph_2SiH_2$. However, a reducing agent ($NaBHEt_3$) is needed, and dihydrodiphenylsilane is not a reaction substrate having high industrial value.

Also an example of reaction by a cobalt-carbonyl complex ($Co_2(CO)_8$ or the like) is reported (Non-Patent Documents 10 to 15); however, this is not satisfactory in terms of reaction yield or reaction molar ratio, and the complex has highly toxic carbon monoxide and the handling and storage of the complex require the conditions of being in an inert gas atmosphere and at low temperature.

Also an example of reaction of olefin with trialkylsilane in the presence of a cobalt-carbonyl complex having a trialkylsilyl group is reported in Non-Patent Document 16, but the yield is low and the selectivity is low.

Non-Patent Document 17 reports reaction of olefin with trialkylsilane in the presence of a cobalt-phosphite complex coordinated with a cyclopentadienyl group, and Non-Patent Document 18 reports reaction of olefin with trihydrophenylsilane in the presence of a cobalt complex coordinated with N-heterocyclic carbene. Because of low stability, these complex compounds require an inert gas atmosphere and a low temperature for handling and storage.

Also an example of reaction by a cobalt catalyst having a β-diketiminate group as a ligand is reported (Non-Patent Document 19); however, when the reaction substrate is trihydrophenylsilane, the industrial utility value is low. Although also an example of reaction between 1-hexene and triethoxysilane is shown, the amount of the catalyst needs to be 2 mol %, and the catalytic activity is not high.

Also an example of reaction by a cobalt catalyst having a pyridinediimine ligand, the precursor of which catalyst is easy to handle, is reported, and the catalyst has high catalytic activity (Non-Patent Document 20); however, in this reaction, also dehydrogenative silylation reaction progresses, and therefore minute amounts of dehydrogenative silylated compounds always coexist; consequently, the selectivity of the addition product is low.

Also a hydrosilylation reaction catalyst using bis(cyclooctatetraenyl)iron and an isocyanide compound as ligands (Non-Patent Document 21) and a hydrosilylation reaction catalyst using iron pivalate or cobalt pivalate and an isocyanide compound as ligands (Non-Patent Document 22) are reported; however, neither is comparable to Pt catalysts in terms of catalytic activity, and the development of a catalyst having higher catalytic activity is desired.

Further, in hydrosilylation reaction using an alkenyl sulfide derivative as an unsaturated compound, the sulfur element acts as a catalytic poison; hence, an example using a Pt catalyst and an example using a Rh catalyst, which are only among few examples of reports, are reported (Non-Patent Documents 23 and 24). However, the catalytic activity is lower than in other substrates, and the selectivity of the addition reaction product is low.

The example using a Rh catalyst reports that an addition product in which Si is bonded to carbon adjacent to the sulfur element is obtained selectively (Non-Patent Document 25); however, the catalytic activity is low, and the selectivity of the adduct is low.

Many examples of the nickel complex catalyst are reported. For example, a catalyst having a phosphine ligand (Non-Patent Document 26) lacks in selectivity and requires careful handling and storage.

With a vinylsiloxane-coordinated catalyst (Non-Patent Document 27), a product due to the dehydrogenative becomes predominant, indicating low selectivity of addition reaction.

With an allylphosphine-coordinated catalyst (Non-Patent Document 28), the yield is low, and trihydrophenylsilane is not a reaction substrate of industrial worth.

A metal bisamide catalyst (Non-Patent Document 29) needs careful handling and storage, and dihydrodiphenylsilane is not a reaction substrate of industrial worth.

A catalyst having N-heterocyclocarbene ligand (Non-Patent Document 30) has low selectivity of reaction, and trihydrophenylsilane is not of industrial worth.

Also Patent Documents 3 to 6 report iron, cobalt and nickel catalysts having terpyridine, bisiminopyridine and bisiminoquinoline ligands. Like the above-cited Non-Patent Documents 6 to 8, there is an industrial difficulty of synthesis of a catalyst precursor or synthesis of the complex catalyst from the precursor.

Patent Document 7 discloses a method of conducting reaction in the presence of a complex catalyst having a bisiminoquinoline ligand, using Mg(butadiene)·2THF or NaEt$_3$BH as the catalyst activator. Likewise, the yield of the desired product is less than satisfactory.

The catalysts with their application to organopolysiloxanes being borne in mind include a catalyst having a phosphine ligand (Patent Document 8), a catalyst having an aryl-alkyl-triazenide group (Patent Document 9), a colloidal catalyst (Patent Document 10), a catalyst coordinated with a sulfide group (Patent Document 11), and a catalyst coordinated with an amino, phosphino or sulfide group and an organosiloxane group (Patent Document 12).

However, reactivity is empirically demonstrated with respect to only platinum, palladium, rhodium and iridium which are expensive metal elements. Thus the method is not regarded cost effective.

In Examples of Patent Documents 13 and 14, only well-known platinum catalysts are demonstrated to exert a catalytic effect while the structure which is combined with another metal to exert catalytic activity is indicated nowhere.

Patent Documents 15 to 17 disclose catalysts coordinated with carbene. Patent Document 15 does not discuss whether or not the catalyst is effective to hydrosilylation reaction.

Patent Documents 16 and 17 disclose catalysts coordinated with carbene and vinylsiloxane, but describe only platinum catalysts in Examples.

In addition, the metal catalysts coordinated with carbene require careful handling because the complex compounds have low storage stability.

Patent Documents 18 to 24 disclose a method of mixing a metal salt with a compound which coordinates to the metal and using the product as a catalyst rather than the use of metal complexes as the catalyst. Although these Patent Documents describe the progress of hydrosilylation with several exemplary combinations, the yield and other data are described nowhere, and the extent to which the reaction takes place is not evident. In addition, ionic salts or hydride reducing agents are used as the activator in all examples. Nevertheless, almost all examples exhibit no catalytic activity.

On the other hand, there are also many reports on hydrogenation reaction in which a hydrogen molecule is added to an olefin, which is a compound having a carbon-carbon double bond. For example, hydrogenation by thermal reaction using Fe(CO)$_5$ as a catalyst (Non-Patent Document 31) and hydrogenation by photoreaction (Non-Patent Document 32) are reported. However, thermal reaction requires conditions of high temperature and high pressure (180° C., 28 atmospheres); in contrast, photoreaction progresses at room temperature; but both have low turnover numbers (TON), which number indicates the number of revolutions of the catalyst, and cannot be said to have sufficient activity.

Further, an example of reaction using an iron catalyst using an organic aluminum compound as a reaction aid (Non-Patent Document 33) and an example of reaction using a Grignard compound or a lithium aluminum hydride compound and an iron chloride catalyst in combination (Non-Patent Documents 34 and 35) are reported; however, the TON is less than or equal to 20, and the catalytic activity is low.

Also an iron catalyst having a phosphorus-based compound as a ligand is reported (Non-Patent Document 36); in this system, although reaction is made under conditions of room temperature and relatively low pressure (4 atmospheres), the turnover number cannot be said to be sufficient.

Also an example of an iron catalyst having a 1,2-bis (dimethylsilyl)benzene ligand is reported (Non-Patent Document 37); in this example, although reaction progresses at room temperature under normal pressure, the synthesis of the catalyst is not easy.

Also an example of an iron catalyst having a bis(imino) pyridine ligand is reported (Non-Patent Document 7), and this example has good reactivity, i.e., a TON of 1,814, under conditions of room temperature and relatively low pressure (4 atmospheres).

Further, an iron catalyst having a 2,6-bis(arylimidazol-2-ylidene)pyridine ligand is reported (Non-Patent Document 38); however, both have points at issue such as safety at the time of synthesis and the stability of the compound, similarly to the Fe complex having a bis(imino)pyridine ligand mentioned above.

Also a cobalt catalyst having a phosphorus-based compound as a ligand is reported (Non-Patent Document 39); in this system, although reaction progresses at room temperature under normal pressure, the synthesis of the catalyst is not easy.

A cobalt catalyst having a bis(mesitylbenzimidazol-2-ylidene)phenyl ligand is reported (Non-Patent Document 40); however, this has points at issue such as safety at the time of synthesis and the stability of the compound, similarly to the Fe complex having a 2,6-bis(arylimidazol-2-ylidene)pyridine ligand mentioned above, and furthermore the catalytic activity cannot be said to be sufficient, in view of the TON being 50.

Further, as methods for reducing compounds having a carbon-oxygen or carbon-nitrogen double bond and a carbon-nitrogen triple bond, there is a method in which hydrogen is used in the presence of a hydrogen compound of aluminum or boron or a noble metal catalyst. Among carbonyl compounds, for ketones and aldehydes, a stable, easy-to-handle hydride reaction agent and a noble metal catalyst for hydrogenation that allow reaction to progress under mild conditions are known; on the other hand, for the reduction of carboxylic acid derivatives such as esters and amides, a method using a strong reducing agent such as lithium aluminum hydride or a borane is mainly used (Non-Patent Document 41). However, these reducing agents are ignitable, water-sensitive substances, and are therefore less easy to handle. Further, care is required in handling also when removing aluminum or a boron compound after reaction from the desired product.

A large number of methods in which a hydrosilane compound or methyl hydrogen polysiloxane, which is stable and easy to handle in air, is used as a reducing agent are reported; however, the reaction requires the addition of a strong acid or a Lewis acid, or the use of an expensive noble metal catalyst. These days, hydrosilane reduction reactions of a carbonyl compound using inexpensive iron, cobalt, or nickel as a catalyst are reported; some examples of them are used for reduction reaction of an amide, for which conventional methods need severe conditions. Specific examples include Non-Patent Documents 37, and 42 to 49; however, a highly active catalyst exhibiting a higher turnover number is desired.

On the other hand, an iron-, cobalt-, or nickel-isocyanide complex is known in Non-Patent Documents 50 to 62; however, these literatures are mainly for the synthesis, structure analysis, and reaction of the complex, and have no example in which the complex is used as a catalyst for hydrosilylation reaction or hydrogenation reaction on an aliphatic unsaturated bond or hydrosilane reduction reaction on a carbon-oxygen unsaturated bond or a carbon-nitrogen unsaturated bond.

PRIOR ART DOCUMENTS

| PATENT DOCUMENTS | |
|---|---|
| Patent Document 1: | WO 2013/081794 |
| Patent Document 2: | WO 2010/016416 |
| Patent Document 3: | JP-A 2012-532885 |
| Patent Document 4: | JP-A 2012-532884 |
| Patent Document 5: | JP-A 2013-544824 |
| Patent Document 6: | JP-A 2014-502271 |
| Patent Document 7: | JP-A 2014-503507 |
| Patent Document 8: | JP-A H06-136126 |
| Patent Document 9: | JP-A H06-263780 |
| Patent Document 10: | JP-A H01-315344 |
| Patent Document 11: | JP 3174616 |
| Patent Document 12: | JP-A H07-149780 |
| Patent Document 13: | JP-A 2001-131231 |
| Patent Document 14: | JP 4007467 |
| Patent Document 15: | JP 3599669 |
| Patent Document 16: | JP 3854151 |
| Patent Document 17: | JP 4249702 |
| Patent Document 18: | WO 2013/043846 |
| Patent Document 19: | WO 2013/043783 |
| Patent Document 20: | WO 2013/043912 |
| Patent Document 21: | WO 2014/021908 |
| Patent Document 22: | WO 2013/081794 |
| Patent Document 23: | WO 2013/043785 |
| Patent Document 24: | WO 2013/043787 |

| NON-PATENT DOCUMENTS | |
|---|---|
| Non-Patent Document 1: | A. N. Nesmeyanov et al., Tetrahedron, 1962, 17, 61 |
| Non-Patent Document 2: | M. S. Wrighton et al., J. Organomet. Chem., 1977, 128, 345 |
| Non-Patent Document 3: | F. Kakiuchi et al., J. Organomet. Chem., 1993, 456, 45 |
| Non-Patent Document 4: | H. Nakazawa et al., J. Am. Chem. Soc., 2012, 134, 804 |
| Non-Patent Document 5: | H. Nakazawa et al., Organometallics, 2012, 31, 3825 |
| Non-Patent Document 6: | P. J. Chirik et al., Organometallics, 2012, 31, 4886 |
| Non-Patent Document 7: | P. J. Chirik et al., J. Am. Chem. Soc., 2004, 126, 13794 |
| Non-Patent Document 8: | P. J. Chirik et al., Science, 2012, 335, 567 |
| Non-Patent Document 9: | J. Chen, et al., Angew. Chem. Int. Ed., 2015, 54, 4661 |
| Non-Patent Document 10: | A. J. Chalk et al., J. Am. Chem. Soc., 1965, 87, 1133 |
| Non-Patent Document 11: | A. J. Chalk et al., J. Am. Chem. Soc., 1967, 89, 1640 |
| Non-Patent Document 12: | A. J. Chalk et al., J. Organomet. Chem., 1970, 21, 207 |
| Non-Patent Document 13: | B. A. Izmailov, et al., J. Organomet. Chem., 1978, 149, 29 |
| Non-Patent Document 14: | N. Sonoda et al., J. Org. Chem., 1987, 52, 4864 |
| Non-Patent Document 15: | S. Murai et al., Chem. Lett., 2000, 14 |
| Non-Patent Document 16: | M. S. Wrighton et al., Inorg. Chem., 1980, 19, 3858 |
| Non-Patent Document 17: | B. E. Grant et al., J. Am. Chem. Soc., 1993, 115, 2151 |
| Non-Patent Document 18: | L. Deng et al., Angew. Chem. Int. Ed., 2013, 52, 10845 |
| Non-Patent Document 19: | P. Hollad, et al., J. Am. Chem. Soc., 2015, 137, 13244 |
| Non-Patent Document 20: | P. J. Chirik, et al., ACS Catal., 2016, 6, 2632 |
| Non-Patent Document 21: | H. Nagashima, et al., Organometallics, 2015, 34, 2896 |
| Non-Patent Document 22: | H. Nagashima, et al., J. Am. Chem. Soc., 2016, 138, 2480 |
| Non-Patent Document 23: | L. V. Vranken, et al., J. Org. Chem., 2001, 66, 7270 |
| Non-Patent Document 24: | S. V. Kirpichenko, et al., J. Organomet. Chem., 1980, 190, 335 |
| Non-Patent Document 25: | S. Kato, et al., Organometallics, 1998, 17, 926 |
| Non-Patent Document 26: | M. Umeno et al., J. Organomet. Chem., 1973, 50, 297 |
| Non-Patent Document 27: | I. Kownacki et al., J. Organomet. Chem., 2000, 597, 175 |
| Non-Patent Document 28: | P. Valerga et al., Dalton Trans., 2007, 3000 |
| Non-Patent Document 29: | T. D. Tilley et al., Chem. Commun., 2012, 48, 7146 |

| NON-PATENT DOCUMENTS | |
|---|---|
| Non-Patent Document 30: | P. Valerga et al., Organometallics, 2012, 31, 2175 |
| Non-Patent Document 31: | E. N. Frankel, et al., J. Org. Chem., 1964, 29, 3292 |
| Non-Patent Document 32: | M. S. Wrighton, et al., J. Am. Chem. Soc., 1976, 98, 551 |
| Non-Patent Document 33: | R. E. Harmon, et al., J. Chem, Rev., 1973, 73, 21 |
| Non-Patent Document 34: | J. G. de Vries, et al., Dalton Trans., 2010, 39, 8464 |
| Non-Patent Document 35: | A. J. Wangelin, et al., Green Chem., 2015, 17, 1408 |
| Non-Patent Document 36: | J. C. Peters, et al., Inorg. Chem., 2004, 43, 7474 |
| Non-Patent Document 37: | H. Nagashima, et al., Chem. Commun., 2011, 47, 6581 |
| Non-Patent Document 38: | P. J. Chirik, et al., ACS Catal., 2012, 2, 1760 |
| Non-Patent Document 39: | J. C. Peters, et al., J. Am. Chem. Soc., 2013, 135, 15310 |
| Non-Patent Document 40: | P. J. Chirik, et al., J. Am. Chem. Soc., 2016, 138, 11907 |
| Non-Patent Document 41: | W. R. Brown, Organic Reactions, 1941, 6, 470 |
| Non-Patent Document 42: | H. Nagashima, et al., Angew. Chem. Int. Ed., 2009, 48, 9511 |
| Non-Patent Document 43: | M. Beller, et al., Angew. Chem. Int. Ed., 2009, 48, 9507 |
| Non-Patent Document 44: | H. Nishiyama, et al., Angew. Chem. Int. Ed., 2010, 49, 9384 |
| Non-Patent Document 45: | H. Nishiyama, et al., Chem. Eur. J., 2010, 16, 3090 |
| Non-Patent Document 46: | M. Beller, et al., Angew. Chem., 2012, 51, 1662 |
| Non-Patent Document 47: | J.-B. Sortais, et al., Adv. Synth. Catal., 2013, 355, 3358 |
| Non-Patent Document 48: | Z. Lu, et al., Chem. Commun., 2015, 5725 |
| Non-Patent Document 49: | T. Murai, et al., J. Org. Chem., 1990, 55, 449 |
| Non-Patent Document 50: | F. G. A. Stone, et al., J. Chem. Soc., Dalton Trans., 1979, 1003 |
| Non-Patent Document 51: | W. C. Wolsey, et al., J. Chem. Soc., Dalton Trans., 1981, 219 |
| Non-Patent Document 52: | N. J. Coville, et al., J. Chem. Soc., Dalton Trans., 1982, 1069 |
| Non-Patent Document 53: | W. D. Jones, et al., Inorg. Chem., 1987, 26, 2120 |
| Non-Patent Document 54: | D. Lentz, J. Organomet. Chem., 1989, 377, 305 |
| Non-Patent Document 55: | J. S. Figueroa, et al., Inorg. Chem., 2015, 54, 5579 |
| Non-Patent Document 56: | Y. Yamamoto, et al., Inorg. Chem., 1978, 17, 3111 |
| Non-Patent Document 57: | P. Woodward, et al., J. Chem. Soc., Dalton Trans., 1980, 80 |
| Non-Patent Document 58: | N. J. Cooper, et al., J. Am. Chem. Soc., 1994, 116, 8566 |
| Non-Patent Document 59: | J. S. Figueroa, et al., J. Am. Chem. Soc., 2010, 132, 5033 |
| Non-Patent Document 60: | E. L. Muetterties, et al., J. Am. Chem. Soc., 1977, 99, 743 |
| Non-Patent Document 61: | E. L. Muetterties, et al., Inorg. Chem., 1980, 19, 1552 |
| Non-Patent Document 62: | D. Lentz, et al., J. Fluorine Chem., 1998, 89, 73 |

SUMMARY OF INVENTION

Technical Problem

The present invention has been made in view of such circumstances, and an object of the present invention is to provide a catalyst that can exhibit excellent catalytic activity in hydrosilylation reaction or hydrogenation reaction on an aliphatic unsaturated bond or hydrosilane reduction reaction on a carbon-oxygen unsaturated bond or a carbon-nitrogen unsaturated bond, and a method for producing various compounds using the catalyst.

Solution to Problem

The present inventors conducted extensive studies in order to achieve the object mentioned above, and have found out that a prescribed iron-, cobalt-, or nickel-isocyanide complex can exhibit excellent catalytic activity in hydrosilylation reaction or hydrogenation reaction on an aliphatic unsaturated bond or hydrosilane reduction reaction on a carbon-oxygen unsaturated bond or a carbon-nitrogen unsaturated bond, and allows each of the reactions mentioned above to progress under mild conditions; thus, have completed the present invention.

The invention provides a catalyst and a method defined below.

1. A catalyst including a compound represented by formula (1) below, and having activity in at least one reaction selected from hydrosilylation reaction or hydrogenation reaction on an aliphatic unsaturated bond and hydrosilane reduction reaction on a carbon-oxygen unsaturated bond or a carbon-nitrogen unsaturated bond, $$M_n(L)_m \tag{1}$$

wherein M represents Fe, Co, or Ni with an oxidation number of 0, L represents an isocyanide ligand represented by formula (2) below, n represents an integer of 1 to 8, and m represents an integer of 2 to 12,

$$(CN)_xR^1 \tag{2}$$

wherein $R^1$ represents a monovalent to trivalent organic group that has 1 to 30 carbon atoms and is optionally substituted with a halogen atom and in which one or more atoms selected from oxygen, nitrogen, sulfur, and silicon are optionally interposed, and x represents an integer of 1 to 3.

2. The catalyst according to 1, wherein, in the formula (2), x is 1.

3. The catalyst according to 1 or 2, wherein, in the formula (1), when n=1, m=2, 4, or 5, and when n=2 to 4, m=an integer of 6 to 10.

4. The catalyst according to any one of 1 to 3, wherein, in the formula (1), when M is Fe, n=1 and m=5, when M is Co, n=2 and m=8, and when M is Ni, n=1 and m=2 or 4, or n=3, 4, or 8 and m=4, 6, 7, or 12.

5. The catalyst according to any one of 1 to 4, wherein M in the formula (1) is Fe or Co.

6. The catalyst according to any one of 1 to 5, wherein $R^1$ in the formula (2) is a monovalent hydrocarbon group having 1 to 30 carbon atoms.

7. The catalyst according to 6, wherein $R^1$ in the formula (2) is at least one hydrocarbon group selected from an alkyl group having 1 to 20 carbon atoms, a cycloalkyl group having 3 to 20 carbon atoms, an aryl group having 6 to 30 carbon atoms, and an alkylaryl group having 7 to 30 carbon atoms.

8. The catalyst according to 7, wherein $R^1$ in the formula (2) is at least one hydrocarbon group selected from a t-butyl group, a 1-adamantyl group, a mesityl group, a phenyl group, a 2,6-dimethylphenyl group, and a 2,6-diisopropylphenyl group.

9. A method for producing a product of hydrosilylation reaction between an aliphatic unsaturated bond-containing compound and a Si—H bond-containing compound, wherein the method uses the catalyst according to any one of 1 to 8.

10. A method for producing a product of hydrogenation reaction of an aliphatic unsaturated bond-containing compound, wherein the method uses the catalyst according to any one of 1 to 8.

11. The production method according to 9 or 10, wherein the aliphatic unsaturated bond-containing compound is an olefin compound, or a silane compound or an organopolysiloxane having an alkenyl group bonded to a Si atom.

12. A method for producing a product of reduction reaction by a Si—H bond-containing compound of a compound having a carbon-oxygen unsaturated bond or a carbon-nitrogen unsaturated bond, wherein the method uses the catalyst according to any one of 1 to 8.

13. The method for producing a product of reduction reaction according to 12, wherein the compound having a carbon-oxygen unsaturated bond or a carbon-nitrogen unsaturated bond is an aldehyde compound, a ketone compound, an amide compound, or a nitrile compound.

Advantageous Effects of Invention

A catalyst for reaction made of an iron-, cobalt-, or nickel-isocyanide complex (hereinafter, simply abbreviated as an isocyanide complex) of the present invention does not have a carbonyl ligand highly toxic to human bodies, and has high thermal stability and high stability in air of the complex.

When the isocyanide complex of the present invention is used as a catalyst to perform hydrosilylation reaction between an aliphatic unsaturated bond-containing compound and a silane or a (poly)siloxane having a Si—H group, addition reaction can be made under conditions of room temperature to less than or equal to 100° C. In particular, also addition reaction with an industrially useful (poly)siloxane, a trialkoxysilane, or a dialkoxysilane progresses well. A known literature shows that, in the same reaction, both addition reaction on an unsaturated bond and reaction that produces an unsaturated bond-containing compound due to dehydrogenative silylation reaction progress simultaneously in many cases; in contrast, when the catalyst of the present invention is used, addition reaction on an unsaturated bond progresses selectively.

In addition, in reaction with an internal olefin, which has been difficult for conventional catalysts, a product of addition reaction accompanied by movement of an unsaturated bond to an end can be obtained.

Further, by using the catalyst of the present invention, in hydrosilylation reaction of an alkenyl sulfide or the like, an addition product in which Si is bonded to carbon adjacent to the sulfur element is obtained selectively.

Further, the catalyst of the present invention has high catalytic activity on hydrogenation reaction of an aliphatic unsaturated bond-containing compound, and the reaction progresses under mild conditions.

Further, in hydrosilane reduction reaction on a carbon-oxygen unsaturated bond or a carbon-nitrogen unsaturated bond using the catalyst of the present invention, a carbonyl compound such as an amide compound, a ketone compound, or an amide compound, or a nitrile compound, and an easy-to-handle silane or (poly)siloxane having a Si—H group are reacted together, and the desired compound can be obtained with a high yield.

Thus, the catalyst made of an isocyanide complex of the present invention has activity on one or a plurality of reactions among hydrosilylation reaction or hydrogenation reaction on an aliphatic unsaturated bond and hydrosilane reduction reaction on a carbon-oxygen unsaturated bond or a carbon-nitrogen unsaturated bond, and is therefore very highly useful in organic synthesis reaction.

DESCRIPTION OF EMBODIMENTS

Below the invention is described in more detail.

The invention provides a catalyst including a compound represented by formula (1) below, and having activity in at least one reaction selected from hydrosilylation reaction or hydrogenation reaction on an aliphatic unsaturated bond and hydrosilane reduction reaction on a carbon-oxygen unsaturated bond or a carbon-nitrogen unsaturated bond.

$$M_n(L)_m \quad (1)$$

In formula (1), M represents Fe, Co, or Ni with an oxidation number of 0, L represents an isocyanide ligand represented by formula (2) below, n represents an integer of 1 to 8, and m represents an integer of 2 to 12.

$$(CN)_x-R^1 \quad (2)$$

In formula (1), as mentioned above, n represents 1 to 4, and m represents 2 to 10; from the viewpoints of the stability of the complex and catalytic activity, it is preferable that, in the case where n is 1, m be 2, 4, or 5; in the case where n=2 to 4, m be an integer of 6 to 10; in the case where n=8, m be 12; it is more preferable that, in the case where M is Fe, n be 1 and m be 5; in the case where M is Co, n be 2 and m be 8; in the case where M is Ni, n be 1 and m be 2 or 4, or n be 3, 4, or 8 and m be 4, 6, 7, or 12.

In formula (2), $R^1$ represents a monovalent to trivalent organic group that has 1 to 30 carbon atoms and is optionally substituted with a halogen atom and in which one or more atoms selected from oxygen, nitrogen, sulfur, and silicon are optionally interposed, and x represents an integer of 1 to 3.

Specific examples of the halogen atom include fluorine, chlorine, bromine, and iodine.

The monovalent to trivalent organic group having 1 to 30 carbon atoms is not particularly limited, but is preferably a monovalent to trivalent hydrocarbon group having 1 to 30 carbon atoms.

Examples of monovalent hydrocarbon groups include alkyl, alkenyl, alkynyl, aryl, alkyl aryl, and aralkyl groups.

The alkyl groups may be straight, branched or cyclic, is preferably 1 to 20, more preferably 1 to 10 alkyl group. Examples include straight or branched alkyl groups such as methyl, ethyl, n-propyl, isopropyl, n-butyl, isobutyl, s-butyl, t-butyl, n-pentyl, n-hexyl, n-heptyl, n-octyl, 2-ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-eicosanyl; and cycloalkyl groups such as cyclopropyl, cyclobutyl, cyclopentyl, cyclohexyl, cycloheptyl, cyclooctyl, cyclononyl, norbornyl, and adamantyl.

The alkenyl group is preferably an alkenyl group having 2 to 20 carbon atoms, and examples include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-1-decenyl, and n-1-eicosenyl.

The alkynyl group is preferably an alkynyl group having 2 to 20 carbon atoms, and examples include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecynyl, and n-1-eicosynyl.

The aryl or alkylaryl group is preferably an aryl group having 6 to 20 carbon atoms or an alkylaryl group having 7 to 20 carbon atoms, and specific examples include phenyl, 1-naphthyl, 2-naphthyl, anthryl, phenanthryl, o-biphenylyl, m-biphenylyl, p-biphenylyl, tolyl, 2,6-dimethylphenyl, 2,6-diisopropylphenyl, a mesityl group, and the like.

The aralkyl group is an arylalkyl group preferably having 7 to 30 carbon atoms and more preferably having 7 to 20 carbon atoms, and specific examples include benzyl, phenylethyl, phenylpropyl, naphthylmethyl, naphthylethyl, a naphthylpropyl group, and the like.

Suitable divalent hydrocarbon groups include alkylene, arylene and aralkylene groups.

The alkylene groups may be straight, branched or cyclic ones, preferably alkylene groups having 1 to 20 carbon atoms. Examples include straight or branched alkylene groups such as methylene, ethylene, propylene, trimethylene, n-butylene, isobutylene, s-butylene, n-octylene, 2-ethylhexylene, n-decylene, n-undecylene, n-dodecylene, n-tridecylene, n-tetradecylene, n-pentadecylene, n-hexadecylene, n-heptadecylene, n-octadecylene, n-nonadecylene, and n-eicosanylene; and cycloalkylene groups such as 1,4-cyclohexylene.

Examples of the arylene group include o-phenylene, m-phenylene, p-phenylene, 1,2-naphthylene, 1,8-naphthylene, 2,3-naphthylene, and 4,4'-biphenylene.

Examples of the aralkylene group include —(CH$_2$)$_y$—Ar— wherein Ar is an arylene group having 6 to 20 carbon atom and y is an integer of 1 to 10, —Ar—(CH$_2$)$_y$— wherein Ar and y are as defined above, and —(CH$_2$)$_y$—Ar—(CH$_2$)$_y$— wherein Ar is as defined above and y is each independently as defined above.

Specific examples of the trivalent hydrocarbon group include those represented by the following formulae, but are not limited to these.

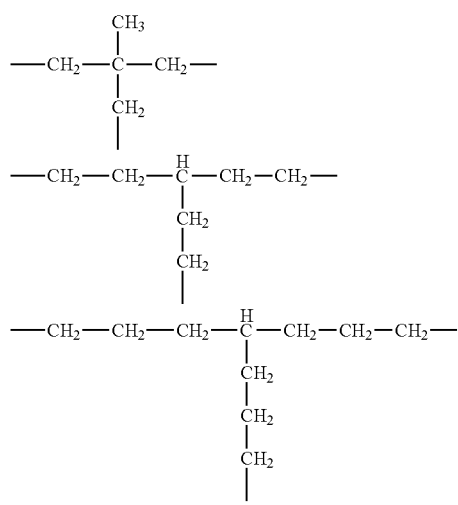

[Chem. 1]

Specific examples of other organic groups in R$^1$ above include alkoxy groups such as a methoxy group, an ethoxy group, a propoxy group, and an isopropoxy group; aryloxy groups such as a phenoxy group; alkyl halide groups such as a trifluoromethyl group; alkylamino groups such as a dimethylamino group; ester groups such as a methyl ester and an ethyl ester; a nitro group; a nitrile group; alkyl- or arylsilyl groups such as a trimethylsilyl group and a phenyldimethylsilyl group; alkoxysilyl groups such as a trimethoxysilyl group, a triethoxysilyl group, a dimethoxymethylsilyl group, and a diethoxymethylsilyl group; nitrogen-containing heterocycle-containing groups such as a pyridyl group; sulfur-containing heterocycle-containing groups such as a thienyl group; and the like.

Among these, R$^1$ is preferably at least one hydrocarbon group selected from an alkyl group having 1 to 20 carbon atoms, a cycloalkyl group having 3 to 20 carbon atoms, an aryl group having 6 to 30 carbon atoms, and an alkylaryl group having 7 to 30 carbon atoms, and is more preferably a t-butyl group, a 1-adamantyl group, a mesityl group, a phenyl group, a 2,6-dimethylphenyl group, and a 2,6-diisopropylphenyl group.

One or more atoms selected from oxygen, nitrogen, silicon, sulfur, and phosphorus may be interposed in each of the organic groups described above, and each of the organic groups described above may be substituted with a halogen atom.

x in formula (2) above represents an integer of 1 to 3, and is preferably 1 or 2 and more preferably 1.

The isocyanide compound represented by formula (2) above may be obtained as a commercially available product, or may be synthesized by a known method. For example, it may be obtained by a method in which a formylated product is obtained from an amine compound and formic acid, and subsequently the formylated product is reacted with phosphoryl chloride in the presence of an organic amine to be turned into an isocyanide (Synthesis Method 1; see Organometallics, 2004, 23, 3976-3981); as a method for obtaining a formylated product under mild conditions, a formylated product can be obtained by forming acetic formic anhydride from acetic anhydride and formic acid, and reacting the acetic formic anhydride with an amine compound (Synthesis Method 2; see Org. Synth., 2013, 90, 358-366). The obtained formylated product can be turned into an isocyanide by the method described in Synthesis Method 1, which is the same as above.

The synthesis can be made also by a method in which an amine compound and dichlorocarbene are reacted together to produce an isocyanide, which is a method not involving formylation (Synthesis Method 3; see Tetrahedron Letters, 1972, 17, 1637-1640).

Examples of the isocyanide compound include alkyl isocyanides such as methyl isocyanide, ethyl isocyanide, n-propyl isocyanide, cyclopropyl isocyanide, n-butyl isocyanide, isobutyl isocyanide, sec-butyl isocyanide, t-butyl isocyanide, n-pentyl isocyanide, isopentyl isocyanide, neopentyl isocyanide, n-hexyl isocyanide, cyclohexyl isocyanide, cycloheptyl isocyanide, 1,1-dimethylhexyl isocyanide, 1-adamantyl isocyanide, and 2-adamantyl isocyanide; aryl isocyanides such as phenyl isocyanide, 2-methylphenyl isocyanide, 4-methylphenyl isocyanide, 2,4-dimethylphenyl isocyanide, 2,5-dimethylphenyl isocyanide, 2,6-dimethylphenyl isocyanide, 2,4,6-trimethylphenyl isocyanide, 2,4,6-tri-t-butylphenyl isocyanide, 2,6-diisopropylphenyl isocyanide, 1-naphthyl isocyanide, 2-naphthyl isocyanide, 2-methyl-1-naphthyl isocyanide; aralkyl isocyanides such as benzyl isocyanide and phenylethyl isocyanide.

Examples of the diisocyanide compound include 1,2-diisocyanoethane, 1,3-diisocyanopropane, 1,4-diisocyanobutane, 1,5-diisocyanopentane, 1,6-diisocyanohexane, 1,8-diisocyanooctane, 1,12-diisocyanododecane, 1,2-diisocyanocyclohexane, 1,3-diisocyanocyclohexane, 1,4-diisocyanocyclohexane, 1,3-diisocyano-2,2-dimethylpropane, 2,5-diisocyano-2,5-dimethylhexane, 1,2-bis(diisocyanoethoxy)ethane, 1,2-diisocyanobenzene, 1,3-diisocyanobenzene, 1,4-diisocyanobenzene, 1,1'-methylenebis(4-isocyanobenzene), 1,1'-oxybis(4-isocyanobenzene), 3-(isocyanomethyl)benzyl isocyanide, 1,2-bis(2-isocyanophenoxy)ethane, bis(2-isocyanophenyl)phenyl phosphonate, bis(2-isocyanophenyl) isophthalate, bis(2-isocyanophenyl) succinate.

Examples of the triisocyanide compound include 1,3-diisocyano-2-(isocyanomethyl)-2-methylpropane, 1,5-diisocyano-3-(2-isocyanoethyl)pentane, 1,7-diisocyano-4-(3-isocyanopropyl)heptane, and 3-isocyano-N,N'-bis(3-isocyanopropyl)propane-1-amine.

A catalyst made of an isocyanide complex represented by formula (1) above can be synthesized by a known method; for example, the synthesis can be made by a method in which an iron, cobalt, or nickel salt and a reducing agent are reacted together in an organic solvent in the presence of an isocyanide compound, or a method in which an iron-, cobalt-, or nickel-carbonyl complex and an isocyanide compound are reacted together in an organic solvent at high temperature under light irradiation or in the presence of a catalyst. The synthesis can be made also by reacting together an iron, cobalt, or nickel complex having a substitutable ligand and an isocyanide compound in an organic solvent.

The synthesis can be made also by reacting together an ate-type iron-, cobalt-, or nickel-isocyanide complex and an oxidizing agent in an organic solvent.

The iron, cobalt, or nickel salt mentioned above is not particularly limited, but is preferably a halide of Cl, Br, I, or the like, or a carboxylate such as acetate, and is more preferably a halide of Cl, Br, I, or the like, in view of reactivity with a reducing agent.

Specific examples of the iron salt include iron halides such as $FeCl_2$, $FeBr_2$, $FeCl_3$, $FeBr_3$, and $FeI_3$; iron carboxylates such as $Fe(OAc)_2$, $Fe(stearate)_2$, and $Fe(stearate)_3$; and the like.

Specific examples of the cobalt salt include cobalt halides such as $CoCl_2$, $CoBr_2$, and $CoI_2$; cobalt carboxylates such as $Co(OAc)_2$, $Co(OBz)_2$, $Co(2\text{-ethylhexanoate})_2$, and $Co(stearate)_2$; and the like.

Specific examples of the nickel salt include nickel halides such as $NiCl_2$, $NiBr_2$, and $NiI_2$; nickel carboxylates such as $Ni(OAc)_2$; and the like.

Specific examples of the iron-, cobalt-, or nickel-carbonyl complex mentioned above include $Fe(CO)_5$, $Fe_3(CO)_{12}$, $Co_2(CO)_8$, $Ni(CO)_4$, and the like.

As the substitutable ligand, olefin compounds such as 1,5-cyclooctadiene and butadienes; phosphorus ligands such as trimethylphosphine; and the like are given.

The reducing agent mentioned above is desirably a strong reducing agent that can reduce a metal in an iron, cobalt, or nickel salt up to zero-valence; for example, is preferably a reducing agent having an oxidation-reduction potential, with ferrocene as a standard, of less than or equal to −2.0 V in Non-Patent Document, Chem. Rev. 1996, 96, 887-910, and is particularly preferably a reducing agent having an oxidation-reduction potential of less than or equal to −2.3 V.

Specific examples include alkali metals such as sodium and potassium; alkali metal alloys such as sodium-potassium and sodium amalgam; alkali metal naphthalenide such as potassium naphthalenide; and the like, but are not limited to these.

Each of these alkali metals and alkali metal alloys may be one supported by a solid substance; examples include sodium, potassium, sodium-potassium alloy, or the like supported by silica, alumina, graphite, titanium oxide, zeolite, zinc oxide, cerium oxide, or polystyrene; among these, potassium-carrying graphite (hereinafter, abbreviated as $KC_8$) is preferable from the viewpoint of reactivity, and sodium-carrying silica (Stage 1 or 2) is preferable in terms of low risk of ignitability etc. from the viewpoint of safety.

An alkali metal supported by any of these solid substances may be obtained as, for example, one synthesized by a conventionally known method such as a method described in JP 5048503B2, or may be obtained as a commercially available product, examples of which include $KC_8$ (manufactured by Strem Chemicals, Inc.), Na silica gel (manufactured by Aldrich Corporation, Stage I), Na silica gel (manufactured by Aldrich Corporation, Stage II), $NaK_2$ silica gel (manufactured by Aldrich Corporation, Stage I), and the like.

The ate-type iron-, cobalt-, or nickel-isocyanide complex mentioned above is generally known as an ionic complex in which an iron-, cobalt-, or nickel-isocyanide complex is further reduced, and $Na[Co(2,6\text{-dimesityl isocyanide})_4]$ described in Non-Patent Document 51 and the like are known.

Ferrocenium triflate or the like is given as an oxidizing agent in the case where the synthesis is made by using an ate-type iron-, cobalt-, or nickel-isocyanide complex.

The isocyanide complex represented by formula (1) of the present invention is not particularly limited, and examples include the following.

Specific examples of iron-isocyanide complexes include $Fe(CNMe)_5$, $Fe(CNEt)_5$, $Fe(CN^nPr)_5$, $Fe(CN^iPr)_5$, $Fe(CN^nBu)_5$, $Fe(CN^tBu)_5$, $Fe(CNCy)_5$, $Fe(CNAd)_5$, $Fe(CNCF_3)_5$, $Fe(CNPh)_5$, $Fe(CNXylyl)_5$, $Fe(CNMes)_5$, $Fe(N_2)[CN\text{-}(2,6\text{-bismesitylphenyl})]_4$, $Fe[CN\text{-}(2\text{-methyl-6-chlorophenyl})]_5$, $Fe[CN\text{-}(3,5\text{-dimethoxyphenyl})]_5$, $Fe_2(CNEt)_9$, and the like.

Specific examples of cobalt-isocyanide complexes include $Co_2(CN^tBu)_8$, $Co_2(CNCy)_8$, $Co_2(CNAd)_8$, $Co_2(CNPh)_8$, $Co_2(CNXylyl)_8$, $Co_2(CNMes)_8$, $Co_2[CN\text{-}(2\text{-methyl-6-chlorophenyl})]_8$, $Co_2[CN\text{-}(3,5\text{-dimethoxyphenyl})]_8$, $Co[CN\text{-}(2,6\text{-bismesitylphenyl})]_4$, and the like.

Specific examples of nickel-isocyanide complexes include $Ni(CNMe)_4$, $Ni(CNEt)_4$, $Ni(CN^tBu)_4$, $Ni_2(CN^tBu)_4$, $Ni_3(CN^tBu)_6$, $Ni(CNCy)_4$, $Ni(CNPh)_4$, $Ni(CNMes)_4$, $Ni(CNXylyl)_4$, $Ni[CN\text{-}(4\text{-MeOC}_6H_4)]_4$, $Ni[CN\text{-}(4\text{-NO}_2C_6H_4)]_4$, $Ni(CNC_6F5)_4$, $Ni_4(CN^tBu)_6$, $Ni_4(CN^tBu)_7$, $Ni_4(CNMe)(CN^tBu)_6$, $Ni_4(CNCy)_7$, $Ni_8(CN^iPr)_{12}$, and the like.

In the above, $^nPr$ represents a n-propyl group, $^iPr$ an isopropyl group, $^nBu$ a n-butyl group, $^tBu$ a t-butyl group, Cy a cyclohexylyl group, Ad an adamantyl group, Ph a phenyl group, Mes a mesityl group, and Xylyl a 2,6-dimethylphenyl group.

When performing reaction using the isocyanide complex of the present invention as a catalyst, the amount of the catalyst used is not particularly limited; however, in view of obtaining the desired product with good yield by progressing reaction under mild conditions of approximately 20 to 100° C., it is preferable that more than or equal to 0.001 mol % of the isocyanide complex be used relative to 1 mol of a compound that is a substrate, it is more preferable that more than or equal to 0.01 mol % be used, and it is even more preferable that more than or equal to 0.05 mol % be used. On the other hand, the upper limit of the amount of the isocyanide complex used is not particularly set, but is approximately 10 mol % relative to 1 mol of the substrate and is preferably 5 mol %, from the economic point of view.

In the reaction using the catalyst of the present invention, a known two-electron donating ligand may be used in combination to the extent that the activity etc. of the catalyst are not impaired. The two-electron donating ligand is not particularly limited, but is preferably a ligand other than a carbonyl group, such as an ammonia molecule, an ether compound, an amine compound, a phosphine compound, a phosphite compound, or a sulfide compound.

The isocyanide compound may be further added to the extent that the activity etc. thereof are not impaired, and the addition amount in this case is preferably approximately 0.1 to 5 molar equivalents relative to the catalyst of the present invention.

The conditions of reaction using the catalyst of the present invention are not particularly limited; usually, the reaction temperature is approximately 10 to 100° C., and preferably 20 to 80° C., and the period of reaction is approximately 1 to 48 hours.

The reaction may be performed without a solvent, or may use an organic solvent as necessary.

In the case where an organic solvent is used, examples of the kind include aliphatic hydrocarbons such as pentane, hexane, heptane, octane, and cyclohexane; ethers such as diethyl ether, diisopropyl ether, dibutyl ether, cyclopentyl methyl ether, tetrahydrofuran, and 1,4-dioxane; aromatic hydrocarbons such as benzene, toluene, xylenes, and mesitylene; and the like.

In the case where an organic solvent is used, the concentration of the catalyst is preferably 0.01 to 10 M and more preferably 0.1 to 5 M as molar concentration (M), in view of catalytic activity and economical efficiency.

The catalyst of the present invention may be used as a catalyst for hydrosilylation reaction or hydrogenation reaction on an aliphatic unsaturated bond or hydrosilane reduction reaction on a carbon-oxygen unsaturated bond or a carbon-nitrogen unsaturated bond.

In the reaction using the catalyst of the present invention, all the components may be collectively added, or components may be added in units of several components.

By using the catalyst of the present invention for hydrosilylation reaction, a product of hydrosilylation reaction between an aliphatic unsaturated bond-containing compound and a Si—H bond-containing compound is obtained.

As the use ratio between the aliphatic unsaturated bond-containing compound and the Si—H bond-containing compound in hydrosilylation reaction, the molar ratio of aliphatic unsaturated bonds/Si—H bonds is 1/10 to 10/1, preferably 1/5 to 5/1, and more preferably 1/3 to 3/1.

Specific examples of the aliphatic unsaturated bond-containing compound include the following.

(1) Carbon-Carbon Unsaturated Bond-Containing Hydrocarbon Compounds

Alkenes such as ethylene, propylene, butylene, isobutylene, hexenes, octenes, decenes, dodecenes, n-hexadecene, isohexadecene, n-octadecene, isooctadecene, norbornene, and trifluoropropene; alkynes such as ethyne, propyne, butynes, pentynes, hexynes, octynes, decynes, dodecynes, hexadecynes, and octadecynes; and aromatic group-containing alkenes such as styrene, 2-methylstyrene, 4-chlorostyrene, 4-methoxystyrene, α-methylstyrene, 4-methyl-α-methylstyrene, and allylbenzene.

(2) Allyl Ether Compounds

Allyl glycidyl ether, allyl glycol, allyl benzyl ether, diethylene glycol monoallyl ether, diethylene glycol allyl methyl ether, polyoxyethylene monoallyl ether, polyoxypropylene monoallyl ether, poly(oxyethylene-oxypropylene) monoallyl ether, polyoxyethylene diallyl ether, polyoxypropylene diallyl ether, poly(oxyethylene-oxypropylene) diallyl ether, and the like.

(3) Nitrogen-Containing Alkene Compounds

Allylamine, N,N-dimethylallylamine, N,N-diethylallylamine, N,N-di(n-propyl)allylamine, N,N-diisopropylallylamine, N,N-di(n-butyl)allylamine, N,N-diisobutylallylamine, N-t-butylallylamine, N-allylcyclohexylamine, N-allylmorpholine, N,N-diallylamine, triallylamine, N-allylaniline, N-vinylcarbazole, N-vinylformamide, N-vinylacetamide, N-vinylpyrrolidone, N-vinylphthalimide, and the like.

(4) Carbon-Carbon Unsaturated Bond-Containing Silane Compounds

Trimethylvinylsilane, triethylvinylsilane, trimethoxyvinylsilane, triethoxyvinylsilane, dimethoxymethylvinylsilane, diethoxymethylvinylsilane, methoxydimethylvinylsilane, ethoxydimethylvinylsilane, trimethoxyallylsilane, triethoxyallylsilane, triisopropoxyvinylsilane, phenyldimethoxyvinylsilane, phenyldiethoxyvinylsilane, diphenylmethoxyvinylsilane, diphenylethoxyvinylsilane, triphenylvinylsilane, triphenylvinylsilane, and the like.

(5) Carbon-Carbon Unsaturated Bond-Containing Siloxane Compounds

Pentamethylvinyldisiloxane, tetramethyldivinyldisiloxane, heptamethylvinyltrisiloxane, dimethyldiphenyldivinyldisiloxane, dimethylvinylsiloxy group-end-capped dimethylpolysiloxane, and a dimethylvinylsiloxy group-end-capped (dimethylsiloxane-diphenylsiloxane) copolymer. A trimethylsiloxy group-end-capped (dimethylsiloxane-methylvinylsiloxane) copolymer, a trimethylsiloxy group-end-capped (dimethylsiloxane-diphenylsiloxane-methylvinylsiloxane) copolymer, a dimethylvinylsiloxy group-end-capped (dimethylsiloxane-methylvinylsiloxane) copolymer, a dimethylvinylsiloxy group-end-capped (dimethylsiloxane-methylvinylsiloxane-diphenylsiloxane) copolymer, a hydroxy group-end-capped (dimethylsiloxane-methylvinylsiloxane) copolymer, α-vinyldimethylpolysiloxane, and the like.

In the aliphatic unsaturated bond-containing compound mentioned above, an unsaturated bond may exist at a molecular end or may exist in the interior, or a plurality of unsaturated bonds may exist in the molecule like in hexadienes and octadienes.

Also an alkene compound having a sulfide group like those shown below may be used as the aliphatic unsaturated bond-containing compound. In this case, unlike a silicon compound in which silicon is bonded to carbon at an end of an alkene, which is known in the case where a platinum catalyst is used, isomerization reaction of an alkene occurs, and a silicon compound in which silicon is bonded onto carbon adjacent to the sulfur element is obtained selectively.

(6) Alkene Compounds Having Sulfide Group

Methyl vinyl sulfide, ethyl vinyl sulfide, n-propyl vinyl sulfide, isopropyl vinyl sulfide, n-butyl vinyl sulfide, phenyl vinyl sulfide, benzyl vinyl sulfide, methyl allyl sulfide, ethyl allyl sulfide, n-propyl allyl sulfide, isopropyl allyl sulfide, n-butyl allyl sulfide, isobutyl allyl sulfide, phenyl allyl sulfide, benzyl allyl sulfide, allyl (n-propyl) disulfide, diallyl sulfide, diallyl disulfide, and the like.

Examples of the Si—H Bond-Containing Compound Include the Following Silanes and Siloxanes (1) Silanes Trimethoxysilane, triethoxysilane, triisopropoxysilane, dimethoxymethylsilane, diethoxymethylsilane, dimethoxyphenylsilane, diethoxyphenylsilane, methoxydimethylsilane, ethoxydimethylsilane, triphenylsilane, diphenyldisilane, phenyltrisilane, diphenylmethylsilane, phenyldimethylsilane, diphenylmethoxysilane, diphenylethoxysilane, and the like.

(2) Siloxanes

Pentamethyldisiloxane, tetramethyldisiloxane, heptamethyltrisiloxane, octamethyltetrasiloxane, dimethyl hydrogen siloxy group-end-capped dimethylpolysiloxane, dimethyl hydrogen siloxy group-end-capped methyl hydrogen polysiloxane, trimethylsiloxy group-end-capped methyl hydrogen polysiloxane, a dimethyl hydrogen siloxy group-end-capped (dimethylsiloxane-diphenylsiloxane) copolymer, a trimethylsiloxy group-end-capped (dimethylsiloxane-methylhydrosiloxane) copolymer, a trimethylsiloxy group-end-capped (dimethylsiloxane-diphenylsiloxane-methylhydrogensiloxane) copolymer, a dimethyl hydrogen siloxy group-end-capped (dimethylsiloxane-methylhydrogensiloxane) copolymer, a dimethyl hydrogen siloxy group-end-capped (dimethylsiloxane-methylhydrogensiloxane-diphenylsiloxane) copolymer, a hydroxy group-end-capped (dimethylsiloxane-methylhydrogensiloxane) copolymer, dimethyl hydrogen siloxy group-one-end-capped dimethylpolysiloxane, and the like.

Further, by reacting together an aliphatic unsaturated bond-containing compound and a hydrogen molecule in the presence of the catalyst of the present invention, a corresponding compound having a saturated bond is obtained.

Specific examples of the aliphatic unsaturated bond-containing compound include compounds similar to those given as examples in hydrosilylation reaction mentioned above.

As a means for introducing a hydrogen molecule into a reaction system in hydrogenation reaction, introduction may be made while gas containing hydrogen molecules is caused to flow or bubble in a reactor, or reaction may be performed in a pressure resistant vessel in which gas containing hydrogen molecules is enclosed. The pressure at this time is not particularly limited, but is preferably 0.1 to 3 MPa and more preferably 0.1 to 2 MPa from the viewpoint of safety.

Further, a product of hydrosilane reduction reaction between a compound having a carbon-oxygen unsaturated bond or a carbon-nitrogen unsaturated bond and a Si—H bond-containing compound is obtained in the presence of the catalyst of the present invention.

In this case, the use ratio between the compound having a carbon-oxygen unsaturated bond or a carbon-nitrogen unsaturated bond and the Si—H bond-containing compound is not particularly limited; however, as the molar ratio, (carbon-oxygen unsaturated bonds or carbon-nitrogen unsaturated bonds)/(Si—H bonds) is preferably 1/10 to 1/1, more preferably 1/5 to 1/1, and still more preferably 1/3 to 1/1.

As the Si—H bond-containing compound used in hydrosilane reduction reaction of a compound having a carbon-oxygen unsaturated bond or a carbon-nitrogen unsaturated bond of the present invention, compounds similar to those shown as examples in hydrosilylation reaction mentioned above are given; in view of reactivity and economical efficiency, among them, aryl group-containing silanes such as phenylsilane, diphenylsilane, and dimethylphenylsilane; a siloxane containing Si—H groups adjacent via an oxygen atom, such as 1,1,3,3-tetramethyldisiloxane, trimethylsiloxy group-end-capped methyl hydrogen polysiloxane, and dimethyl hydrogen siloxy group-end-capped methyl hydrogen polysiloxane, are preferable, and 1,1,3,3-tetramethyldisiloxane, 1,1,1,3,3-pentamethyldisiloxane, 1,1,1,3,5,5,5-heptamethyltrisiloxane, trimethylsiloxy group-end-capped methyl hydrogen polysiloxane, and dimethyl hydrogen siloxy group-end-capped methyl hydrogen polysiloxane are more preferable.

As the compound having a carbon-oxygen unsaturated bond or a carbon-nitrogen unsaturated bond that can be used for hydrosilane reduction reaction, a compound having an aldehyde, ketone, amide, or nitrile group, and the like are given; by reacting any of these compounds with a silane or a siloxane containing a Si—H group in the presence of the catalyst of the present invention and performing known post-treatment, the compound can be turned into a respective corresponding amine or alcohol compound.

Specific examples of the compound having a carbon-oxygen unsaturated bond or a carbon-nitrogen unsaturated bond include acetophenone, N,N-dimethylbenzamide, acetonitrile, and the like.

EXAMPLES

Synthesis Examples, Examples and Comparative Examples are given below by way of illustration and not by way of limitation.

All solvents were deoxygenated and dehydrated by well-known methods before they were used in the preparation of catalysts.

The catalysts obtained were stored in a nitrogen gas atmosphere at 25° C. until they were used in reaction.

Hydrosilylation reaction and solvent purification were always carried out in an inert gas atmosphere. The solvents and other ingredients were purified, dried and deoxygenated by well-known methods before they were used in various reactions.

The measurement of $^1$H-NMR was performed using JNM-ECA600 and JNM-LA400 manufactured by JEOL Ltd, and IR measurement was performed using FT/IR-550 manufactured by JASCO Corporation.

In the chemical structure formulae shown below, hydrogen atoms are omitted in accordance with common expression.

[Synthesis Example 1] Synthesis of Cobalt Isocyanide Complex $Co_2(CN^tBu)_8$

Cobalt iodide (0.31 g, 1.0 mmol), tetrahydrofuran (hereinafter, abbreviated as THF) (15 mL), t-butyl isocyanide (0.33 g, 4.0 mmol), and $KC_8$(manufactured by Strem Chemicals, Inc., 0.27 g, 2.0 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in pentane (approximately 40 mL), and the insoluble matter was removed by celite filtration. The filtrate was cooled to −35° C. to perform recrystallization; thus, $Co_2(CN^tBu)_8$ was obtained (0.24 g, 61%).

$^1$H-NMR (600 MHz, $C_6D_6$) δ: 1.44 (s, 72H).

IR (ATR): v=1666 (CN (bridge)), 2093, 1977, 1942 (CN (terminal)) $cm^{-1}$

Anal. Calcd. for $C_{40}H_{72}N_8Co_2$:
C: 61.36; H: 9.27; N: 14.31; Found: C: 61.06; H: 9.52; N: 14.05.

[Synthesis Example 2] Synthesis of Cobalt Isocyanide Complex $Co_2(CNAd)_8$ 0.31 g (1.0 mmol) of cobalt iodide, 0.65 g (4.0 mmol) of 1-isocyanoadamantane (hereinafter, abbreviated as CNAd), THF (15 mL), and $KC_8$ (0.27 g, 2.0 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in toluene (approximately 20 ml), and celite filtration was performed again. The solvent of the filtrate was distilled under reduced pressure, and then the dried substance was washed with a small amount of benzene (approximately 3 ml); thus, $Co_2(CNAd)_8$ was obtained (0.33 g, 47%).
$^1$H-NMR (396 MHz, $C_6D_6$) δ:
2.32 (s, 48H), 2.06 (s, 24H), 1.71 (d, J=10.3, 24H),
1.58 (d, J=10.3, 24H).
IR (ATR): v=1647 (CN (bridge)), 2101, 2000, 1954 (CN (terminal)) $cm^{-1}$
Anal. Calcd. for $C_{88}H_{120}N_8Co_2$:
C: 75.08; H: 8.59; N: 7.96; Found: C: 75.16; H: 8.62; N: 7.46.

[Synthesis Example 3] Synthesis of Cobalt Isocyanide Complex $Co_2(CNMes)_8$

Cobalt iodide (13 mg, 0.10 mmol), mesityl isocyanide (58 mg, 0.40 mmol), THF (3 mL), and $KC_8$ (27 mg, 0.20 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in toluene (approximately 3 mL), and the insoluble matter was removed by celite filtration. Pentane (approximately 3 mL) was slowly added from above the filtrate to perform recrystallization; thus, a cobalt isocyanide complex of $Co_2(CNMes)_8$ was obtained (42 mg, 66%).
$^1$H-NMR (396 MHz, $C_6D_6$) δ:
6.60 (s, 12H), 6.58 (s, 4H), 2.46 (s, 36H), 2.42 (s, 12H), 2.05 (s, 18H), 2.03 (s, 6H).
IR (ATR): v=1669 (CN (bridge)), 2063, 2026, 1954 (CN (terminal)) $cm^{-1}$
Anal. Calcd. for $C_{80}H_{88}N_8Co_2$:
C: 75.10; H: 6.93; N: 8.60; Found: C: 75.21; H: 6.90; N: 8.60.

[Synthesis Example 4] Synthesis of Iron Isocyanide Complex $Fe(CN^tBu)_5$

Iron bromide (22 mg, 0.10 mmol), THF (3 mL), t-butyl isocyanide (42 mg, 0.50 mmol), and $KC_8$ (27 mg, 0.20 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in pentane (approximately 4 mL), and the insoluble matter was removed by celite filtration. The filtrate was cooled to −35° C. to perform recrystallization; thus, $Fe(CN^tBu)_5$ was obtained (30 mg, 63%).

$^1$H-NMR (600 MHz, $C_6D_6$) δ: 1.29 (s, 45H).
IR (ATR): v=2119, 2000, 1943, 1826 (CN) $cm^{-1}$

[Synthesis Example 5] Synthesis of Iron Isocyanide Complex $Fe(CNAd)_5$ Using Iron Bromide and $KC_8$ Iron bromide (216 mg, 1.0 mmol), THF (20 mL), adamantyl isocyanide (806 mg, 5.0 mmol), and $KC_8$ (manufactured by Strem Chemicals, Inc., 270 mg, 2.0 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in benzene (approximately 5 mL), and the insoluble matter was removed by celite filtration. Pentane was added to the filtrate, and then cooling was performed to −35° C. to perform recrystallization; thus, $Fe(CNAd)_5$ was obtained (601 mg, yield: 70%).
$^1$H-NMR (396 MHz, $C_6D_6$) δ:
2.15 (s, 30H), 1.88 (s, 15H), 1.50 (d, J=11.5, 15H), 1.42 (d, J=11.5, 15H).
IR (ATR): v=2106 (CN) $cm^{-1}$

[Synthesis Example 6] Synthesis of Nickel Isocyanide Complex $Ni(CNtBu)_4$ Using Nickel Bromide (Dimethoxyethane Adduct) and $KC_8$ Nickel bromide (a dimethoxyethane adduct) (31 mg, 0.1 mmol), THF (3 mL), t-butyl isocyanide (0.33 g, 0.4 mmol), and $KC_8$ (270 mg, 2.0 mmol) were added in this order to a reactor, and stirring was performed at room temperature for 30 minutes. After that, the reaction solution was subjected to celite filtration, and the solvent of the filtrate was distilled under reduced pressure. The resulting dried substance was dissolved in benzene (approximately 5 mL), and the insoluble matter was removed by celite filtration. Ether was added to the filtrate, and then cooling was performed to −35° C. to perform recrystallization; thus, $Ni(CN^tBu)_4$ was obtained (21 mg, yield: 54%).
$^1$H-NMR (396 MHz, $C_6D_6$) δ: 1.09 (s, 36H).
IR (ATR): v=2002 (CN) $cm^{-1}$

[1] Hydrosilylation Reaction Using Alkene as Substrate

[Example 1] Hydrosilylation Reaction by 1,1,1,3,3-pentamethyldisiloxane of α-methylstyrene Using $Co_2(CN^tBu)_8$ as Catalyst $Co_2(CN^tBu)_8$ obtained in Synthesis Example 1 (3.4 mg, 0.005 mmol), α-methylstyrene (129 μL, 1.0 mmol), and 1,1,1,3,3-pentamethyldisiloxane (254 μL, 1.3 mmol) were added to a reactor, and stirring was performed at 25° C. for 24 hours. After the reaction ended, $^1$H-NMR spectrum was measured to determine the structure and the yield of the product. A multiplet at 0.94 ppm, which is a signal of protons on carbon adjacent to silicon in the desired product, was observed, and the yield was found. The results are shown in Table 1.
$^1$H-NMR (396 MHz, $CDCl_3$) δ:
7.27 (t, J=6.8, 2H), 7.21 (d, J=6.8, 2H), 7.15 (t, J=6.8, 1H),
2.91 (sext, J=6.8, 1H), 1.28 (d, J=6.8, 3H), 0.90-0.98 (m, 2H),
0.05 (s, 9H), −0.05 (s, 3H), −0.07 (s, 3H).

Examples 2 and 3

Reaction was performed in a similar manner to Example 1 except that, in place of $Co_2(CN^tBu)_8$, the cobalt-isocyanide complexes written in Table 1 (each 0.005 mmol) were used as catalysts. The results are shown in Table 1 below.

Comparative Example 1

Hydrosilylation Reaction by 1,1,1,3,3-pentamethyldisiloxane of α-methylstyrene Using, as Catalyst, Composition Consisting of Cobalt Pivalate, CNAd, and Diethoxymethylsilane 3 mg (0.01 mmol) of cobalt pivalate, 5 mg (0.03 mmol) of CNAd, and 100 μL of THF were added to a reactor, and were dissolved. 5.3 mg (0.04 mmol) of diethoxymethylsilane was added to the reactor, and stirring was performed at 25° C. for 1 hour. After that, α-methylstyrene (129 μL, 1.0 mmol) and 1,1,1,3,3-pentamethyldisiloxane (254 μL, 1.3 mmol) were added, and stirring was performed at 25° C. for 24 hours. After the reaction ended, $^1$H-NMR spectrum was measured to determine the structure and the yield of the product. A multiplet at 0.94 ppm, which is a signal of protons on carbon adjacent to silicon in the desired product, was observed, and the yield was found. The results are shown in Table 1.

TABLE 1

| Catalyst | Conversion (%) | Yield (%) |
|---|---|---|
| Example 1 | $Co_2(CN^tBu)_8$ | >99 | >99 |
| Example 2 | $Co_2(CNAd)_8$ | >99 | >99 |
| Example 3 | $Co_2(CNMes)_8$ | >99 | >99 |
| Comparative Example 1 | cobalt pivalate /CNAd/ diethoxymethylsilane | 10 | 10 |

[Example 4] Hydrosilylation Reaction by 1,1,1,3,3-pentamethyldisiloxane of α-methylstyrene Using $Co_2(CNAd)_8$ as Catalyst $Co_2(CNAd)_8$ obtained in Synthesis Example 2 (6.4 mg, 0.0005 mmol), α-methylstyrene (1.29 mL, 10 mmol), and 1,1,1,3,3-pentamethyldisiloxane (2.54 mL, 13 mmol) were added to a reactor, and stirring was performed at 80° C. for 24 hours. After the reaction ended, $^1$H-NMR spectrum was measured to determine the structure and the yield of the product. A multiplet at 0.94 ppm, which is a signal of protons on carbon adjacent to silicon in the desired product, was observed, and the yield was found. The results are shown in Table 2.

Comparative Example 2

Hydrosilylation Reaction by 1,1,1,3,3-pentamethyldisiloxane of α-methylstyrene Using $Co_2(CO)_8$ as Catalyst $Co_2(CO)_8$ (1.7 mg, 0.0005 mmol), α-methylstyrene (1.29 mL, 10 mmol), and 1,1,1,3,3-pentamethyldisiloxane (2.54 mL, 13 mmol) were added to a reactor, and stirring was performed at 80° C. for 24 hours. After the reaction ended, $^1$H-NMR spectrum was measured to determine the structure and the yield of the product. A multiplet at 0.94 ppm, which is a signal of protons on carbon adjacent to silicon in the desired product, was observed, and the yield was found. The results are shown in Table 2.

TABLE 2

| Catalyst | Conversion (%) | Yield (%) |
|---|---|---|
| Example 4 | $Co_2(CNAd)_8$ | >99 | >99 |
| Comparative Example 2 | $Co_2(CO)_8$ | 88 | 88 |

[Example 5] Hydrosilylation Reaction by 1,1,1,3,3-pentamethyldisiloxane of Styrene Using $Fe(CN^tBu)_5$ as Catalyst $Fe(CN^tBu)_5$ obtained in Synthesis Example 4 (4.7 mg, 0.01 mmol), styrene (114 μL, 1.0 mmol), and 1,1,1,3,3-pentamethyldisiloxane (254 μL, 1.3 mmol) were added to a reactor, and stirring was performed at 25° C. for 24 hours. After the reaction ended, $^1$H-NMR spectrum was measured to determine the structure and the yield of the product. A multiplet at 0.90 ppm, which is a signal of protons on carbon adjacent to silicon in the desired product, was observed, and the yield was found. The results are shown in Table 3.
$^1$H-NMR (396 MHz, $CDCl_3$) δ:
7.24-7.29 (m, 2H), 7.13-7.22 (m, 3H), 2.61-2.68 (m, 2H), 0.86-0.92 (m, 2H), 0.08 (s, 9H), 0.07 (s, 6H).

[Example 6] Hydrosilylation Reaction by 1,1,1,3,3-pentamethyldisiloxane of 1-octene Using $Co_2(CNMes)_8$ as Catalyst $Co_2(CNMes)_8$ obtained in Synthesis Example 3 (6.4 mg, 0.005 mmol), 1-octene (157 μL, 1.0 mmol), and 1,1,1,3,3-pentamethyldisiloxane (254 μL, 1.3 mmol) were added to a reactor, and stirring was performed at 25° C. for 24 hours. After the reaction ended, $^1$H-NMR spectrum was measured to determine the structure and the yield of the product. A multiplet at 0.50 ppm, which is a signal of protons on carbon adjacent to silicon in the desired product, was observed, and the yield was found. The results are shown in Table 3.
$^1$H-NMR (396 MHz, $CDCl_3$) δ:
1.21-1.37 (m, 12H), 0.88 (t, J=6.8, 3H), 0.50 (m, 2H), 0.06 (s, 9H), 0.03 (s, 6H).

[Example 7] Hydrosilylation Reaction by 1,1,1,3,3-pentamethyldisiloxane of Styrene Using $Co_2(CNMes)_8$ as Catalyst $Co_2(CNMes)_8$ obtained in Synthesis Example 3 (6.4 mg, 0.005 mmol), styrene (114 μL, 1.0 mmol), and 1,1,1,3,3-pentamethyldisiloxane (254 μL, 1.3 mmol) were added to a reactor, and stirring was performed at 25° C. for 24 hours. After the reaction ended, $^1$H-NMR spectrum was measured to determine the structure and the yield of the product. A multiplet at 0.90 ppm, which is a signal of protons on carbon adjacent to silicon in the desired product, was observed, and the yield was found. The results are shown in Table 3.
$^1$H-NMR (396 MHz, $CDCl_3$) δ:
7.24-7.29 (m, 2H), 7.13-7.22 (m, 3H), 2.61-2.68 (m, 2H), 0.86-0.92 (m, 2H), 0.08 (s, 9H), 0.07 (s, 6H).

[Example 8] Hydrosilylation Reaction by 1,1,1,3,3-pentamethyldisiloxane of Allyl Glycidyl Ether Using $Co_2(CNAd)_8$ as Catalyst $Co_2(CNAd)_8$ obtained in Synthesis Example 2 (6.4 mg, 0.005 mmol), allyl glycidyl ether (118 μL, 1.0 mmol), and 1,1,1,3,3-pentamethyldisiloxane (254 μL, 1.3 mmol) were added to a reactor, and stirring was performed at 25° C. for 24 hours. After the reaction ended, $^1$H-NMR spectrum was measured to determine the structure and the yield of the product. A multiplet at 0.51 ppm, which is a signal of protons on carbon adjacent to silicon in the desired product, was observed, and the yield was found. The results are shown in Table 3.

$^1$H-NMR (396 MHz, CDCl$_3$) δ:

3.71 (dd, J=11.6, J=3.9, 1H) 3.37-3.51 (m, 3H), 3.26 (dt, J=2.9, J=6.3, 1H), 2.62 (t, J=4.4, 1H), 2.62 (q, J=2.9, 1H), 1.59-1.65 (m, 2H), 0.49-0.53 (m, 2H), 0.06 (s, 9H).

TABLE 3

|  | Alkene | Catalyst | Conversion (%) | Yield (%) |
|---|---|---|---|---|
| Example 5 | styrene | Fe(CN$^t$Bu)$_5$ | >99 | 99 |
| Example 6 | 1-octene | Co$_2$(CNMes)$_8$ | >99 | 24 |
| Example 7 | styrene | Co$_2$(CNMes)$_8$ | 90 | 44 |
| Example 8 | allyl glycidyl ether | Co$_2$(CNAd)$_8$ | >99 | 90 |

[Example 9] Hydrosilylation Reaction by 1,1,1,3,5,5,5-heptamethyltrisiloxane of α-methylstyrene Using Co$_2$(CN$^t$Bu)$_8$ as Catalyst Co$_2$(CN$^t$Bu)$_8$ obtained in Synthesis Example 1 (3.4 mg, 0.005 mmol), α-methylstyrene (129 μL, 1.0 mmol), and 1,1,1,3,5,5,5-heptamethyltrisiloxane (351 μL, 1.3 mmol) were added to a reactor, and stirring was performed at 80° C. for 24 hours. After the reaction ended, $^1$H-NMR spectrum was measured to determine the structure and the yield of the product. A multiplet at 0.88 ppm, which is a signal of protons on carbon adjacent to silicon in the desired product, was observed, and the yield was found. The results are shown in Table 4.

$^1$H-NMR (396 MHz, CDCl$_3$) δ:

7.27 (t, J=6.8, 2H), 7.21 (d, J=6.8, 2H), 7.16 (t, J=6.8, 1H), 2.92 (sext, J=6.8, 1H), 1.28 (d, J=6.8, 3H), 0.82-0.94 (m, 2H), 0.09 (s, 9H), 0.07 (s, 9H), −0.12 (s, 3H).

[Example 10] Hydrosilylation Reaction by Triethoxysilane of α-methylstyrene Using Co$_2$(CNAd)$_8$ as Catalyst Co$_2$(CNAd)$_8$ obtained in Synthesis Example 2 (6.4 mg, 0.005 mmol), α-methylstyrene (129 μL, 1.0 mmol), and triethoxysilane (213 mg, 1.3 mmol) were added to a reactor, and stirring was performed at 80° C. for 24 hours. After the reaction ended, $^1$H-NMR spectrum was measured to determine the structure and the yield of the product. A sextet at 3.00 ppm, which is a signal of protons on carbon adjacent to a phenyl group in the desired product, was observed, and the yield was found. The results are shown in Table 4.

$^1$H-NMR (396 MHz, CDCl$_3$) δ:

7.27 (t, J=6.8, 2H), 7.21 (d, J=6.8, 2H), 7.15 (t, J=6.8, 1H), 3.73 (q, J=6.8, 6H), 2.96 (sext, J=6.8, 1H), 1.31 (d, J=6.8, 3H), 1.18 (m, J=6.8, 9H), 1.03 (d, J=6.8, 2H).

[Example 11] Hydrosilylation Reaction by diethoxy(methyl)silane of α-methylstyrene Using Co$_2$(CN$^t$Bu)$_8$ as Catalyst Co$_2$(CN$^t$Bu)$_8$ obtained in Synthesis Example 1 (3.4 mg, 0.005 mmol), α-methylstyrene (129 μL, 1.0 mmol), and diethoxy(methyl)silane (175 mg, 1.3 mmol) were added to a reactor, and stirring was performed at 50° C. for 24 hours. After the reaction ended, $^1$H-NMR spectrum was measured to determine the structure and the yield of the product. A sextet at 2.96 ppm, which is a signal of protons on carbon adjacent to a phenyl group in the desired product, was observed, and the yield was found. The results are shown in Table 4.

$^1$H-NMR (396 MHz, CDCl$_3$) δ:

7.27 (t, J=6.8, 2H), 7.21 (d, J=6.8, 2H), 7.15 (t, J=6.8, 1H), 3.63-3.70 (m, 4H), 3.00 (sext, J=6.8, 1H), 1.32 (d, J=6.8, 3H), 1.21 (t, J=6.8, 3H), 1.15 (t, J=6.8, 3H), 1.03 (d, J=6.8, 2H), −0.08 (s, 3H).

TABLE 4

|  | Silane | Catalyst | Conversion (%) | Yield (%) |
|---|---|---|---|---|
| Example 9 | 1,1,1,3,5,5,5-heptamethyltrisiloxane | Co$_2$(CN$^t$Bu)$_8$ | >99 | >99 |
| Example 10 | triethoxysilane | Co$_2$(CNAd)$_8$ | 84 | 45 |
| Example 11 | Diethoxy(methyl)silane | Co$_2$(CN$^t$Bu)$_8$ | >99 | 92 |

[Example 12] Hydrosilylation Reaction by Polydimethylsiloxane Endblocked at Both Terminals by Dimethylhydrogensiloxy Groups of Allyl Glycidyl Ether Using Co$_2$(CNAd)$_8$ as Catalyst Co$_2$(CNAd)$_8$ obtained in Synthesis Example 2 (6.4 mg, 0.005 mmol), allyl glycidyl ether (154 μL, 1.3 mmol), and polydimethylsiloxane endblocked at both terminals by dimethylhydrogensiloxy groups (degree of polymerization 18) (0.74 g, 0.50 mmol) were added to a reactor, and stirring was performed at 50° C. for 24 hours. After the reaction ended, $^1$H-NMR spectrum was measured to determine the structure and the yield of the product. A multiplet at 0.54 ppm, which is a signal of protons on carbon adjacent to silicon in the desired product, was observed, and the yield was found (yield >99%).

$^1$H-NMR (396 MHz, CDCl$_3$) δ:

3.70 (m, 1H), 2.95-2.90 (m, 2H), 3.45 (m, 3H), 3.15 (m, 1H), 2.80 (m, 1H), 2.61 (m, 1H), 1.62 (m, 2H), 0.54 (m, 2H), 0.08 (br), 0.05 (s), −0.08 (s).

[2] Hydrosilylation Reaction Using Sulfur-Containing Alkene as Substrate

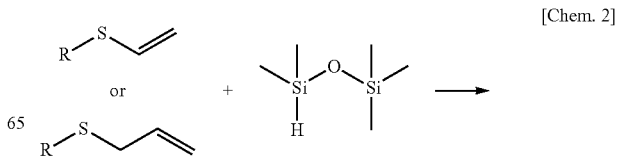

[Chem. 2]

-continued

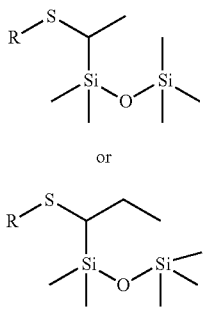

[Example 13] Hydrosilylation Reaction by 1,1,1,3,3-pentamethyldisiloxane of Ethyl Vinyl Sulfide Using $Co_2(CN^tBu)_8$ as Catalyst $Co_2(CN^tBu)_8$ obtained in Synthesis Example 1 (3.4 mg, 0.005 mmol), ethyl vinyl sulfide (88 mg, 1.0 mmol), and 1,1,1,3,3-pentamethyldisiloxane (254 μL, 1.3 mmol) were added to a reactor, and stirring was performed at 25° C. for 24 hours. After the reaction ended, isolation and purification were performed by silica gel chromatography, and 239 mg of the desired product was obtained. Yields are shown in Table 5.

$^1$H-NMR (400 MHz, $CDCl_3$) δ:
0.08 (s, 9H, —$SiMe_3$), 0.12 (s, 3H), 0.16 (s, 3H), 0.98 (t, J=7.32 Hz, 3H), 1.50-1.65 (m, 3H), 1.68-1.71 (m, 1H), 1.75-1.81 (m, 1H), 2.49 (t, 2H).

[Example 14] Hydrosilylation reaction by 1,1,1,3,3-pentamethyldisiloxane of Phenyl Vinyl Sulfide Using $Co_2(CN^tBu)_8$ as Catalyst $Co_2(CN^tBu)_8$ obtained in Synthesis Example 1 (6.0 mg, 0.0075 mmol), phenyl vinyl sulfide (68 mg, 0.5 mmol), and 1,1,1,3,3-pentamethyldisiloxane (223 mg, 1.5 mmol) were added to a reactor, and stirring was performed at 25° C. for 24 hours. After the reaction ended, isolation and purification were performed by Kugelrohr distillation, and 129 mg of the desired product was obtained. Yields are shown in Table 5.

$^1$H-NMR (400 MHz, $CDCl_3$)
δ: 0.11 (s, 9H), 0.18 (s, 3H), 0.20 (s, 3H), 1.31 (d, J=7.73 Hz, 3H),
2.54 (q, J=7.09 Hz, 1H), 7.28 (dd, J=7.73, 9.67 Hz, 1H), 7.28 (d, J=7.73 Hz, 2H), 7.35 (d, J=9.67 Hz, 2H).

[Example 15] Hydrosilylation Reaction by 1,1,1,3,3-pentamethyldisiloxane of Methyl Allyl Sulfide Using $Co_2(CN^tBu)_8$ as Catalyst $Co_2(CN^tBu)_8$ obtained in Synthesis Example 1 (3.4 mg, 0.005 mmol), methyl allyl sulfide (88 mg, 1.0 mmol), and 1,1,1,3,3-pentamethyldisiloxane (254 μL, 1.3 mmol) were added to a reactor, and stirring was performed at 25° C. for 24 hours. After the reaction ended, isolation and purification were performed by silica gel chromatography, and 209 mg of the desired product was obtained. Yields are shown in Table 5.

$^1$H-NMR (400 MHz, $CDCl_3$) δ:
0.08 (s, 9H), 0.13 (s, 3H), 0.16 (s, 3H), 1.06 (t, J=7.14 Hz, 3H),
1.57-1.62 (m, 2H), 1.75-1.81 (m, 1H), 2.09 (s, 3H).

[Example 16] Hydrosilylation Reaction by 1,1,1,3,3-pentamethyldisiloxane of n-Propyl Allyl Sulfide Using $Co_2(CN^tBu)_8$ as Catalyst $Co_2(CN^tBu)_8$ obtained in Synthesis Example 1 (3.4 mg, 0.005 mmol), n-propyl allyl sulfide (116 mg, 1.0 mmol), and 1,1,1,3,3-pentamethyldisiloxane (254 μL, 1.3 mmol) were added to a reactor, and stirring was performed at 25° C. for 24 hours. After the reaction ended, isolation and purification were performed by silica gel chromatography, and 239 mg of the desired product was obtained. Yields are shown in Table 5.

$^1$H-NMR (400 MHz, $CDCl_3$) δ:
0.08 (s, 9H), 0.12 (s, 3H), 0.16 (s, 3H), 0.98 (t, J=7.32 Hz, 3H),
1.50-1.65 (m, 3H), 1.68-1.71 (m, 1H), 1.75-1.81 (m, 1H), 2.49 (t, 2H).

[Example 17] Hydrosilylation Reaction by 1,1,1,3,3-pentamethyldisiloxane of Phenyl Allyl Sulfide Using $Co_2(CN^tBu)_8$ as Catalyst $Co_2(CN^tBu)_8$ obtained in Synthesis Example 1 (9.7 mg, 0.0125 mmol), phenyl allyl sulfide (75 mg, 0.5 mmol), and 1,1,1,3,3-pentamethyldisiloxane (127 μL, 0.65 mmol) were added to a reactor, and stirring was performed at 25° C. for 24 hours. After the reaction ended, isolation and purification were performed by Kugelrohr distillation, and 142 mg of the desired product was obtained. Yields are shown in Table 5.

$^1$H-NMR (600 MHz, $CDCl_3$) δ:
0.10 (s, 9H), 0.19 (s, 3H), 0.19 (s, 3H), 1.31 (t, J=7.42 Hz, 3H),
1.67 (dqd, J=6.04, 7.42, 13.74 Hz, 1H),
1.81 (dqd, 6.04, 7.42, 13.74 Hz, 1H), 7.14 (td, J=7.42, 2.75 Hz, 1H),
7.25-7.26 (m, 2H), 7.35 (dd, J=8.24, 1.10 Hz, 2H).

[Example 18] Hydrosilylation Reaction by 1,1,1,3,3-pentamethyldisiloxane of Benzyl Allyl Sulfide Using $Co_2(CN^tBu)_8$ as Catalyst $Co_2(CN^tBu)_8$ obtained in Synthesis Example 1 (3.4 mg, 0.005 mmol), benzyl allyl sulfide (164 mg, 1.0 mmol), and 1,1,1,3,3-pentamethyldisiloxane (254 μL, 1.3 mmol) were added to a reactor, and stirring was performed at 25° C. for 24 hours. After the reaction ended, isolation and purification were performed by Kugelrohr distillation, and 245 mg of the desired product was obtained. Yields are shown in Table 5.

$^1$H-NMR (400 MHz, $CDCl_3$) δ:
0.05 (s, 9H), 0.06 (s, 3H), 1.01 (t, J=7.32 Hz, 3H), 1.53-1.62 (m, 1H),
1.63-1.67 (m, 1H), 1.69-1.80 (m, 1H), 3.66-3.75 (m, 2H), 7.22-7.30 (m, 5H).

Comparative Example 3

Hydrosilylation Reaction by 1,1,1,3,3-pentamethyldisiloxane of Methyl Allyl Sulfide Using $Co_2(CO)_8$ as Catalyst $Co_2(CN^tBu)_8$ obtained in Synthesis Example 1 (3.4 mg, 0.005 mmol), methyl allyl sulfide (88 mg, 1.0 mmol), and 1,1,1,3,3-pentamethyldisiloxane (254 μL, 1.3 mmol) were added to a reactor, and stirring was performed at 25° C. for 24 hours. After the reaction ended, $^1$H-NMR spectrum was measured; as a result, only the source material was observed, and a product was not seen (a yield of 0%).

TABLE 5
| | Sulfur-containing alkene | Product | Conversion (%) | Yield (%) | Isolated yield (%) |
|---|---|---|---|---|---|
| Example 13 | | | >99 | >99 | 90 |
| Example 14 | | | >99 | >99 | 90 |
| Example 15 | | | >99 | >99 | 89 |
| Example 16 | | | >99 | >99 | 90 |
| Example 17 | | | >99 | 97 | 95 |
| Example 18 | | | >99 | >99 | 92 |
[3] Hydrosilylation Reaction Using Nitrogen-Containing Alkene as Substrate
[Chem. 3]
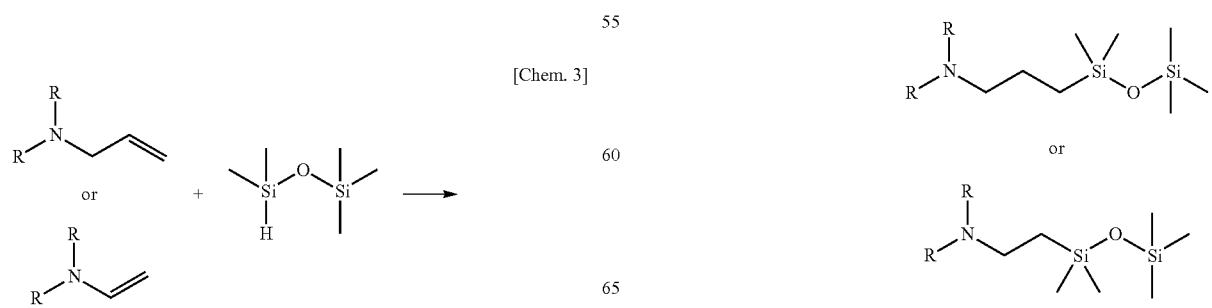

[Example 19] Hydrosilylation Reaction by 1,1,1,3,3-pentamethyldisiloxane of N-Allylaniline Using Co$_2$(CNAd)$_8$ as Catalyst Co$_2$(CNAd)$_8$ obtained in Synthesis Example 2 (6.4 mg, 0.005 mmol), N-allylaniline (133 mg, 1.0 mmol), and 1,1,1,3,3-pentamethyldisiloxane (254 µL, 1.3 mmol) were added to a reactor, and stirring was performed at 25° C. for 24 hours. After the reaction ended, $^1$H-NMR spectrum was measured to determine the structure and the yield of the product. A multiplet at 0.59 ppm, which is a signal of protons on carbon adjacent to silicon in the desired product, was observed, and the yield was found. The results are shown in Table 6.

$^1$H-NMR (400 MHz, CDCl$_3$) δ:
0.07 (s, 15H), 0.59 (m, 2H), 1.63 (m, 2H), 3.10 (q, J=5.8, 2H),
3.66 (br, 1H), 6.60 (d, J=7.7, 2H), 6.68 (t, J=7.7, 1H), 7.17 (t, J=7.2, 2H).

[Example 20] Hydrosilylation Reaction by 1,1,1,3,3-pentamethyldisiloxane of N,N-Diethylallylamine Using Co$_2$(CNAd)$_8$ as Catalyst Co$_2$(CNAd)$_8$ obtained in Synthesis Example 2 (6.4 mg, 0.005 mmol), N,N-diethylallylamine (113 mg, 1.0 mmol), and 1,1,1,3,3-pentamethyldisiloxane (254 µL, 1.3 mmol) were added to a reactor, and stirring was performed at 50° C. for 24 hours. After the reaction ended, $^1$H-NMR spectrum was measured to determine the structure and the yield of the product. A multiplet at 0.46 ppm, which is a signal of protons on carbon adjacent to silicon in the desired product, was observed, and the yield was found. The results are shown in Table 6.

$^1$H-NMR (400 MHz, CDCl$_3$) δ:
0.03 (s, 9H), 0.04 (s, 3H), 0.05 (s, 3H), 0.46 (m, 2H), 1.02 (t, J=7.4, 6H),
1.47 (m, 2H), 2.40 (t, J=8.0, 2H), 2.52 (q, J=7.4, 4H).

[Example 21] Hydrosilylation Reaction by 1,1,1,3,3-pentamethyldisiloxane of 9-vinylcarbazole Using Co$_2$(CNMes)$_8$ as Catalyst Co$_2$(CNMes)$_8$ obtained in Synthesis Example 3 (6.4 mg, 0.005 mmol), N-methyl pyrrolidone (100 µL) as a solvent, 9-vinylcarbazole (193 mg, 1.0 mmol), and 1,1,1,3,3-pentamethyldisiloxane (254 µL, 1.3 mmol) were added to a reactor, and stirring was performed at 25° C. for 24 hours. After the reaction ended, $^1$H-NMR spectrum was measured to determine the structure and the yield of the product. A multiplet at 1.16 ppm, which is a signal of protons on carbon adjacent to silicon in the desired product, was observed, and the yield was found. The results are shown in Table 6.

$^1$H-NMR (400 MHz, CDCl$_3$) δ:
0.15 (s, 6H), 0.17 (s, 9H), 1.16 (m, 2H), 4.38 (m, 2H), 7.23 (t, J=7.7 Hz, 2H), 7.39 (d, J=7.7 Hz, 2H), 7.47 (t, J=7.7 Hz, 2H),
8.11 (d, J=7.7 Hz, 2H).

[Example 22] Hydrosilylation Reaction by 1,1,1,3,3-pentamethyldisiloxane of N-vinylphthalimide Using Co$_2$(CN$^t$Bu)$_8$ as Catalyst Co$_2$(CN$^t$Bu)$_8$ obtained in Synthesis Example 1 (3.4 mg, 0.005 mmol), DME (100 µL) as a solvent, N-vinylphthalimide (173 mg, 1.0 mmol), and 1,1,1,3,3-pentamethyldisiloxane (254 µL, 1.3 mmol) were added to a reactor, and stirring was performed at 50° C. for 24 hours. After the reaction ended, $^1$H-NMR spectrum was measured to determine the structure and the yield of the product. A multiplet at 1.03 ppm, which is a signal of protons on carbon adjacent to silicon in the desired product, was observed, and the yield was found. The results are shown in Table 6.

$^1$H-NMR (400 MHz, CDCl$_3$) δ:
0.07 (s, 9H), 0.14 (s, 6H), 1.03 (m, 2H), 3.75 (m, 2H), 7.69-7.80 (m, 4H).

[Example 23] Hydrosilylation Reaction by 1,1,1,3,3-pentamethyldisiloxane of N-vinyl-2-pyrrolidone Using Co$_2$(CNAd)$_8$ as Catalyst Co$_2$(CNAd)$_8$ obtained in Synthesis Example 2 (6.4 mg, 0.005 mmol), N-vinyl-2-pyrrolidone (111 mg, 1.0 mmol), and 1,1,1,3,3-pentamethyldisiloxane (254 µL, 1.3 mmol) were added to a reactor, and stirring was performed at 50° C. for 24 hours. After the reaction ended, $^1$H-NMR spectrum was measured to determine the structure and the yield of the product. A multiplet at 0.81 ppm, which is a signal of protons on carbon adjacent to silicon in the desired product, was observed, and the yield was found. The results are shown in Table 6.

$^1$H-NMR (400 MHz, CDCl$_3$) δ:
0.08 (s, 9H), 0.10 (s, 6H), 0.82 (m, 2H), 2.00 (quint, J=7.2, 2H),
2.36 (t, J=7.7, 2H), 3.36 (m, 4H).

Comparative Example 4

Hydrosilylation Reaction by 1,1,1,3,3-pentamethyldisiloxane of N-vinyl-2-pyrrolidone Using Co$_2$(CO)$_8$ as Catalyst Co$_2$(CO)$_8$ (1.7 mg, 0.005 mmol), N-vinyl-2-pyrrolidone (111 mg, 1.0 mmol), and 1,1,1,3,3-pentamethyldisiloxane (254 µL, 1.3 mmol) were added to a reactor, and stirring was performed at 50° C. for 24 hours. After the reaction ended, $^1$H-NMR spectrum was measured to determine the structure and the yield of the product. A multiplet at 0.81 ppm, which is a signal of protons on carbon adjacent to silicon in the desired product, was observed, and the yield was found. The results are shown in Table 6.

TABLE 6

| | Nitrogen-containing alkene | Product | Catalyst | Conversion (%) | Yield (%) |
|---|---|---|---|---|---|
| Example 19 | [structure] | [structure] | Co$_2$(CNAd)$_8$ | >99 | 41 |

TABLE 6-continued

| | Nitrogen-containing alkene | Product | Catalyst | Conversion (%) | Yield (%) |
|---|---|---|---|---|---|
| Example 20 | | | Co$_2$(CNAd)$_8$ | >99 | 73 |
| Example 21 | | | Co$_2$(CNMes)$_8$ | >99 | 90 |
| Example 22 | | | Co$_2$(CN$^t$Bu)$_8$ | 60 | 52 |
| Example 23 | | | Co$_2$(CNAd)$_8$ | >99 | 82 |
| Comparative Example 4 | | | Co$_2$(CO)$_8$ | <1 | <1 |

[4] Hydrosilane Reduction Reaction Using, as Substrate, Compound Having Carbon-Oxygen Unsaturated Bond or Carbon-Nitrogen Unsaturated Bond

[Example 24] Hydrosilane Reduction Reaction by Dimethylphenylsilane of Acetophenone Using Co$_2$(CN$^t$Bu)$_8$ as Catalyst

[Chem. 4]

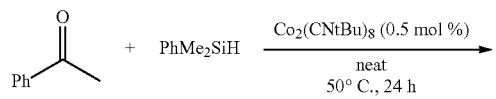

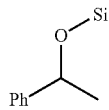

Co$_2$(CN$^t$Bu)$_8$ obtained in Synthesis Example 1 (3.4 mg, 0.005 mmol), acetophenone (120 mg, 1.0 mmol), and dimethylphenylsilane (177 mg, 1.3 mmol) were added to a reactor, and stirring was performed at 50° C. for 24 hours. After the reaction ended, $^1$H-NMR spectrum was measured to determine the structure and the yield of the product. The results are shown in Table 7.

$^1$H-NMR (400 MHz, CDCl$_3$):

0.28 (s, 3H), 0.33 (s, 3H), 1.42 (d, J=6.4 Hz), 4.85 (q, 6.4 Hz, 1H), 7.16-7.41 (m, 8H), 7.53-7.59 (m, 2H).

[Example 25] Hydrosilane Reduction Reaction by 1,1,3,3-tetramethyldisiloxane of Acetophenone Using Fe(CN$^t$Bu)$_5$ as Catalyst

[Chem. 5]

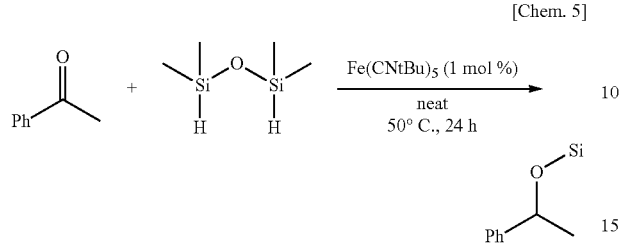

Fe(CN$^t$Bu)$_5$ obtained in Synthesis Example 4 (4.7 mg, 0.01 mmol), acetophenone (120 mg, 1.0 mmol), and 1,1,3,3-tetramethyldisiloxane (147 mg, 1.3 mmol) were added to a reactor, and stirring was performed at 50° C. for 24 hours. After the reaction ended, $^1$H-NMR spectrum was measured to determine the structure and the yield of the product. The results are shown in Table 7.

1:1 adduct (a); $^1$H-NMR (400 MHz, CDCl$_3$):
0.02 (s, 3H), 0.10 (s, 3H), 0.13 (d, J=3.0, 3H), 0.14 (d, J=3.0, 3H),
1.46 (d, J=6.5 Hz, 3H), 4.66 (m, 1H), 4.98 (q, 6.4 Hz, 1H), 7.19-7.37 (m, 5H).

1:2 adduct (b); $^1$H-NMR (400 MHz, CDCl$_3$):
0.05-0.17 (m, 12H), 1.44 (d, J=6.5 Hz, 6H), 4.94 (q, 6.4 Hz, 2H),
7.19-7.37 (m, 10H).

Comparative Example 5

Hydrosilane Reduction Reaction by 1,1,3,3-tetramethyldisiloxane of Acetophenone Using Fe$_2$(CO)$_9$ as Catalyst Fe$_2$(CO)$_5$ (1.8 mg, 0.005 mmol), acetophenone (120 mg, 1.0 mmol), and 1,1,3,3-tetramethyldisiloxane (147 mg, 1.3 mmol) were added to a reactor, and stirring was performed at 50° C. for 24 hours. After the reaction ended, $^1$H-NMR spectrum was measured to determine the structure and the yield of the product. The results are shown in Table 7.

TABLE 7

| | Hydrosilane | Structure of product | Catalyst | Yield (%) |
|---|---|---|---|---|
| Example 24 | dimethylphenylsilane | [O-SiMe$_2$Ph on PhCH(CH$_3$)] | Co$_2$(CNAd)$_8$ | >99 |
| Example 25 | 1,1,3,3-tetramethyldisiloxane | a + b | Fe(CN$^t$Bu)$_5$ | 52 (a:b = 1:1) |
| Comparative Example 5 | 1,1,3,3-tetramethyldisiloxane | a + b | Fe$_2$(CO)$_9$ | 8 (a:b = 3:1) |

[Example 26] Hydrosilane Reduction Reaction by Diphenylsilane of N,N-dimethylbenzamide Using Co$_2$(CNMes)$_8$ as Catalyst

[Chem. 6]

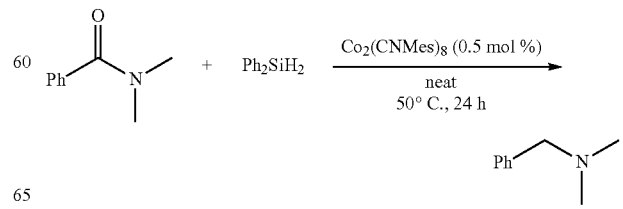

Co$_2$(CNMes)$_8$ obtained in Synthesis Example 3 (6.4 mg, 0.005 mmol), N,N-dimethylbenzamide (149 mg, 1.0 mmol), and diphenylsilane (239 mg, 1.3 mmol) were added to a reactor, and stirring was performed at 50° C. for 24 hours. After the reaction ended, $^1$H-NMR spectrum was measured to determine the structure and the yield of the product. The results are shown in Table 8.

$^1$H-NMR (400 MHz, CDCl$_3$): 2.24 (s, 6H), 3.42 (s, 2H), 7.30-7.38 (m, 5H).

[Example 27] Hydrosilane Reduction Reaction by 1,1,3,3-tetramethyldisiloxane of N,N-dimethylbenzamide Using Fe(CN$^t$Bu)$_5$ as Catalyst

[Chem. 7]

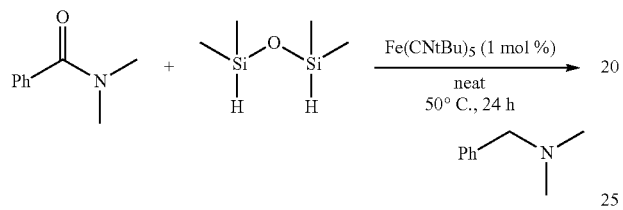

Fe(CN$^t$Bu)$_5$ obtained in Synthesis Example 4 (4.7 mg, 0.01 mmol), N,N-dimethylbenzamide (149 mg, 1.0 mmol), and 1,1,3,3-tetramethyldisiloxane (147 mg, 1.3 mmol) were added to a reactor, and stirring was performed at 50° C. for 24 hours. After the reaction ended, $^1$H-NMR spectrum was measured to determine the structure and the yield of the product. The results are shown in Table 8.

Comparative Example 6

Hydrosilane reduction reaction by diphenylsilane of N,N-dimethylbenzamide using Co$_2$(CO)$_8$ as catalyst Co$_2$(CO)$_8$ (1.7 mg, 0.005 mmol), N,N-dimethylbenzamide (149 mg, 1.0 mmol), and diphenylsilane (239 mg, 1.3 mmol) were added to a reactor, and stirring was performed at 50° C. for 24 hours. After the reaction ended, $^1$H-NMR spectrum was measured to determine the structure and the yield of the product. The results are shown in Table 8.

TABLE 8

| | Hydrosilane | Catalyst | Yield (%) |
|---|---|---|---|
| Example 26 | diphenylsilane | Co$_2$(CNMes)$_8$ | 98 |
| Example 27 | 1,1,3,3-tetramethyldisiloxane | Fe(CN$^t$Bu)$_5$ | 38 |
| Comparative Example 6 | diphenylsilane | Co$_2$(CO)$_8$ | 2 |

[Example 28] Hydrosilane Reduction Reaction by 1,1,3,3-tetramethyldisiloxane of Acetonitrile Using Co$_2$(CN$^t$Bu)$_8$ as Catalyst

[Chem. 8]

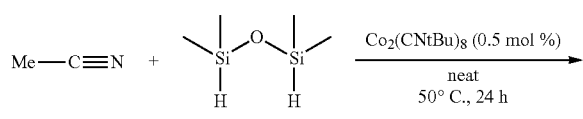

-continued

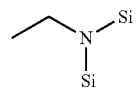

Co$_2$(CN$^t$Bu)$_8$ obtained in Synthesis Example 1 (3.4 mg, 0.005 mmol), acetonitrile (41 mg, 1.0 mmol), and 1,1,3,3-tetramethyldisiloxane (147 mg, 1.3 mmol) were added to a reactor, and stirring was performed at 50° C. for 24 hours. After the reaction ended, a $^1$H-NMR spectrum was measured to determine the structure and the yield of the product. The results are shown in Table 9.

$^1$H-NMR (400 MHz, CDCl$_3$):

0.18 (s, 6H), 0.19 (s, 6H), 1.02 (t, J=6.4, 3H), 2.88 (q, J=6.4, 2H).

Comparative Example 7

Hydrosilane Reduction Reaction by 1,1,3,3-tetramethyldisiloxane of Acetonitrile Using Co$_2$(CO)$_8$ as Catalyst Co$_2$(CO)$_8$ (1.7 mg, 0.005 mmol), acetonitrile (41 mg, 1.0 mmol), and 1,1,3,3-tetramethyldisiloxane (147 mg, 1.3 mmol) were added to a reactor, and stirring was performed at 50° C. for 24 hours. After the reaction ended, $^1$H-NMR spectrum was measured to determine the structure and the yield of the product. The results are shown in Table 9.

TABLE 9

| | Product | Catalyst | Yield (%) |
|---|---|---|---|
| Example 28 | | Co$_2$(CN$^t$Bu)$_8$ | 98 |
| Comparative Example 7 | | Co$_2$(CO)$_8$ | <1 |

[5] Hydrogenation Reaction Using Compound Having Carbon-Carbon Unsaturated Bond as Substrate

[Example 29] Hydrogenation Reaction of 1-octene Using Co$_2$(CN$^t$Bu)$_8$ as Catalyst Co$_2$(CN$^t$Bu)$_8$ obtained in Synthesis Example 1 (6.4 mg, 0.005 mmol) and 1-octene (1.12 g, 10 mmol) were added to a reactor for an autoclave, hydrogen at 10 atm. was introduced, and stirring was performed at 80° C. for 24 hours. After the reaction ended, $^1$H-NMR spectrum was measured to determine the structure and the yield of the product. The results are shown in Table 10.

$^1$H-NMR (CDCl$_3$, 400 MHz): δ=0.88 (t, J=7.2 Hz, 6H), 1.16-1.36 (m, 12H).

[Example 30] Hydrogenation Reaction of Styrene Using Fe(CN$^t$Bu)$_5$ as Catalyst Fe(CN$^t$Bu)$_5$ obtained in Synthesis Example 4 (4.7 mg, 0.01 mmol) and styrene (1.04 g, 10 mmol) were added to a reactor for an autoclave, hydrogen at 10 atm. was introduced, and stirring was performed at 80° C. for 24 hours. After the reaction ended, $^1$H-NMR spectrum was measured to determine the structure and the yield of the product. The results are shown in Table 10.

$^1$H-NMR (CDCl$_3$, 400 MHz):

δ=1.13 (t, J=7.2 Hz, 3H), 2.54 (q, J=7.2 Hz, 2H), 7.02-7.20 (m, 5H)

TABLE 10

| | Alkene | Catalyst | Product | Yield (%) | TON |
|---|---|---|---|---|---|
| Example 29 | 1-octene | Co$_2$(CN$^t$Bu)$_8$ | octane | >99 | 1,000 |
| Example 30 | styrene | Fe(CN$^t$Bu)$_5$ | ethyl benzene | 22 | 220 |

[Example 31] Hydrosilylation Reaction by Triethylsilane of α-methylstyrene Using Co$_2$(CN$^t$Bu)$_8$ as Catalyst Co$_2$(CN$^t$Bu)$_8$ obtained in Synthesis Example 1 (3.4 mg, 0.005 mmol), α-methylstyrene (129 μL, 1.0 mmol), and triethylsilane (151 mg, 1.3 mmol) were added to a reactor, and stirring was performed at 25° C. for 24 hours. After the reaction ended, $^1$H-NMR spectrum was measured to determine the structure and the yield of the product. A multiplet of 2.86 ppm in the desired product was observed, and the yield was found. The results are shown in Table 11.

$^1$H-NMR (396 MHz, CDCl$_3$) δ:

7.21-7.27 (m, 4H), 7.15-7.17 (m, 1H), 2.86 (sext, J=6.8, 1H)

1.27 (d, J=6.8, 3H), 0.98 (dd, J=14.8, 6.8 Hz, 1H)

0.90 (dd, J=14.8, 6.8 Hz, 1H), 0.86 (t, J=8.0, 9H), 0.34-0.48 (m, 6H)

[Example 32] Hydrosilylation Reaction by Dimethylphenylsilane of α-methylstyrene Using Co$_2$(CN$^t$Bu)$_8$ as Catalyst Co$_2$(CN$^t$Bu)$_8$ obtained in Synthesis Example 1 (3.4 mg, 0.005 mmol), α-methylstyrene (129 μL, 1.0 mmol), and dimethylphenylsilane (177 mg, 1.3 mmol) were added to a reactor, and stirring was performed at 25° C. for 24 hours. After the reaction ended, $^1$H-NMR spectrum was measured to determine the structure and the yield of the product. A multiplet of 2.85 ppm in the desired product was observed, and the yield was found. The results are shown in Table 11.

$^1$H-NMR (396 MHz, CDCl$_3$) δ:

7.44-7.47 (2H, m), 7.31-7.34 (3H, m), 7.21-7.26 (2H, m)

7.11-7.17 (3H, m), 2.85 (sext, J=6.8, 1H), 1.23 (d, J=6.8, 3H)

1.22 (dd, J=14.8, 6.8 Hz, 1H), 1.15 (dd, J=14.8, 6.8 Hz, 1H)

0.15 (s, 3H), 0.09 (s, 3H)

TABLE 11

| | Silane | Catalyst | Conversion (%) | Yield (%) |
|---|---|---|---|---|
| Example 31 | triethylsilane | Co$_2$(CN$^t$Bu)$_8$ | >99 | >99 |
| Example 32 | dimethylphenylsilane | Co$_2$(CN$^t$Bu)$_8$ | >99 | >99 |

[Example 33] Hydrosilylation Reaction by Polydimethylsiloxane Endblocked at Both Terminals by Dimethylhydrogensiloxy Groups of α-methylstyrene Using Co$_2$(CNAd)$_8$ as Catalyst Co$_2$(CNAd)$_8$ obtained in Synthesis Example 2 (6.4 mg, 0.005 mmol), α-methylstyrene (1.53 mg, 13 mmol), and polydimethylsiloxane endblocked at both terminals by dimethylhydrogensiloxy groups (degree of polymerization 18) (7.4 g, 5.0 mmol) were added to a reactor, and stirring was performed at 50° C. for 24 hours. After the reaction ended, $^1$H-NMR spectrum was measured to determine the structure and the yield of the product. A multiplet at 0.98 ppm, which is a signal of protons on carbon adjacent to silicon in the desired product, was observed, and the yield was found (yield >99%).

$^1$H-NMR (396 MHz, CDCl$_3$) δ:

7.27 (t, J=6.8, 2H), 7.21 (d, J=6.8, 2H), 7.15 (t, J=6.8, 1H)

2.92 (sext, J=6.8, 1H), 1.28 (d, J=6.8, 3H), 0.90-0.98 (m, 2H)

0.05 (s), −0.05 (s), −0.07 (s)

[Example 34] Hydrosilylation Reaction by 1,1,1,3,3-pentamethyldisiloxane of α-methylstyrene Using, as a Catalyst, Substance Obtained by Allowing Co$_2$(CNMes)$_8$ to Stand in Air for 24 Hours Co$_2$(CNMes)$_8$ obtained in Synthesis Example 3 (6.4 mg, 0.005 mmol) was added to a reactor in a glove box. The reactor was taken out of the glove box, and was allowed to stand in air at room temperature for 24 hours. After that, the reactor was brought into the glove box, α-methylstyrene (129 μL, 1.0 mmol) and 1,1,1,3,3-pentamethyldisiloxane (254 μL, 1.3 mmol) were added to the reactor, and stirring was performed at 25° C. for 24 hours. After the reaction ended, $^1$H-NMR spectrum was measured to determine the structure and the yield of the product. A multiplet at 0.94 ppm, which is a signal of protons on carbon adjacent to silicon in the desired product, was observed, and the yield was found (yield >99%).

[Example 35] Hydrosilylation Reaction by 1,1,1,3,3-pentamethyldisiloxane of Styrene Using Fe(CNAd)$_5$ as Catalyst Fe(CNAd)$_5$ obtained in Synthesis Example 5 (8.6 mg, 0.01 mmol), styrene (114 μL, 1.0 mmol), and 1,1,1,3,3-pentamethyldisiloxane (254 μL, 1.3 mmol) were added to a reactor, and stirring was performed at 50° C. for 24 hours. After the reaction ended, $^1$H-NMR spectrum was measured to determine the structure and the yield of the product. A multiplet at 0.90 ppm, which is a signal of protons on carbon adjacent to silicon in the desired product, was observed, and the yield was found. The results are shown in Table 12.

[Example 36] Hydrosilylation Reaction by diethoxy(methyl)silane of Styrene Using Fe(CNAd)$_5$ as Catalyst Fe(CNAd)$_5$ obtained in Synthesis Example 5 (8.6 mg, 0.01 mmol), styrene (114 μL, 1.0 mmol), and diethoxy (methyl)silane (175 mg, 1.3 mmol) were added to a reactor, and stirring was performed at 50° C. for 24 hours. After the reaction ended, $^1$H-NMR spectrum was measured to determine the structure and the yield of the product. A multiplet at 0.90 ppm, which is a signal of protons on carbon adjacent to silicon in the desired product, was observed, and the yield was found. The results are shown in Table 12.

$^1$H-NMR (396 MHz, CDCl$_3$) δ:
7.20 (m, 5H), 3.80 (m, 4H) 2.68-2.72 (m, 2H), 1.23 (t, J=6.8, 6H)
0.97-1.01 (m, 2H), 0.12 (s, 3H)

TABLE 12

|  | Silane | Catalyst | Conversion (%) | Yield (%) |
|---|---|---|---|---|
| Example 35 | 1,1,1,3,3-pentamethyldisiloxane | Fe(CNAd)$_5$ | >99 | >99 |
| Example 36 | diethoxy(methyl)silane | Fe(CNAd)$_5$ | >99 | >99 |

[Example 37] Hydrosilylation Reaction by Polydimethylsiloxane Endblocked at Both Terminals by Dimethylhydrogensiloxy Groups of Styrene Using Fe(CNAd)$_5$ as Catalyst Fe(CNAd)$_5$ obtained in Synthesis Example 5 (8.6 mg, 0.01 mmol), styrene (154 μL, 1.3 mmol), and polydimethylsiloxane endblocked at both terminals by dimethylhydrogensiloxy groups (degree of polymerization 18) (0.74 g, 0.50 mmol) were added to a reactor, and stirring was performed at 50° C. for 24 hours. After the reaction ended, $^1$H-NMR spectrum was measured to determine the structure and the yield of the product. A multiplet at 0.90 ppm, which is a signal of protons on carbon adjacent to silicon in the desired product, was observed, and the yield was found. The results are shown in Table 13.

$^1$H-NMR (396 MHz, CDCl$_3$) δ:
7.24-7.29 (m, 2H), 7.13-7.22 (m, 3H), 2.61-2.68 (m, 2H)
0.86-0.92 (m, 2H), 0.08 (s), 0.07 (s)

TABLE 13

|  | Conversion of Si—H (%) | Yield (%) |
|---|---|---|
| Example 37 | >99 | >99 |

[Example 38] Hydrosilylation Reaction by 1,1,1,3,3-pentamethyldisiloxane of Styrene Using Ni(CN$^t$Bu)$_4$ as Catalyst Ni(CN$^t$Bu)$_4$ obtained in Synthesis Example 6 (3.9 mg, 0.01 mmol), styrene (114 μL, 0.01 mmol), and 1,1,1,3,3-pentamethyldisiloxane (254 μL, 1.3 mmol) were added to a reactor, and stirring was performed at 80° C. for 24 hours. After the reaction ended, $^1$H-NMR spectrum was measured to determine the structure and the yield of the product. A multiplet at 2.65 ppm, which is a signal of protons on carbon adjacent to silicon in the desired product, was observed, and the yield was found (yield: 39%).

$^1$H-NMR (396 MHz, CDCl$_3$) δ:
7.22-7.29 (m, 5H), 2.65 (q, J=7.6 Hz, 1H), 1.35 (d, J=7.6 Hz, 2H)
0.01 (s, 9H), −0.01 (s, 3H), −0.02 (s, 3H)

[Example 39] Hydrosilylation Reaction by 1,1,1,3,3-pentamethyldisiloxane of 1,1,1,3,3-pentamethyl-3-vinyldisiloxane Using Co$_2$(CNMes)$_8$ as Catalyst Co$_2$(CNMes)$_8$ obtained in Synthesis Example 3 (6.4 mg, 0.005 mmol), 1,1,1,3,3-pentamethyl-3-vinyldisiloxane (174 mg, 1.0 mmol), and 1,1,1,3,3-pentamethyldisiloxane (254 μL, 1.3 mmol) were added to a reactor, and stirring was performed at 80° C. for 3 hours. After the reaction ended, $^1$H-NMR spectrum was measured to determine the structure and the yield of the product. A multiplet at 0.40 ppm, which is a signal of protons on carbon adjacent to silicon in the desired product, was observed, and the yield was found. The results are shown in Table 14.

$^1$H-NMR (396 MHz, CDCl$_3$) δ: 0.03 (s, 12H), 0.06 (s, 18H), 0.40 (s, 4H).

[Example 40] Hydrosilylation Reaction by 1,1,1,3,3-pentamethyldisiloxane of Vinyltriethoxysilane Using Co$_2$(CN$^t$Bu)$_8$ as Catalyst Co$_2$(CN$^t$Bu)$_8$ obtained in Synthesis Example 1 (3.4 mg, 0.005 mmol), vinyltriethoxysilane (190 mg, 1.0 mmol), and 1,1,1,3,3-pentamethyldisiloxane (254 μL, 1.3 mmol) were added to a reactor, and stirring was performed at 50° C. for 24 hours. After the reaction ended, $^1$H-NMR spectrum was measured to determine the structure and the yield of the product. A multiplet at 0.50 ppm, which is a signal of protons on carbon adjacent to silicon in the desired product, was observed, and the yield was found. The results are shown in Table 14.

$^1$H-NMR (396 MHz, CDCl$_3$) δ:
3.78 (6H, q, J=7.0 Hz), 1.19 (9H, t, J=7.0 Hz), 0.47-0.53 (4H, m)
0.02 (9H, s), 0.00 (6H, s)

[Chem. 9]

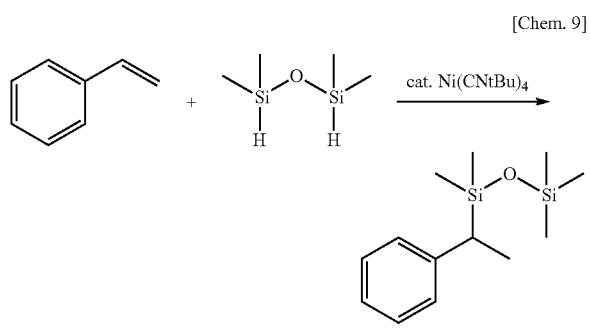

TABLE 14

|  | Alkene | Catalyst | Conversion (%) | Yield (%) |
|---|---|---|---|---|
| Example 39 | 1,1,1,3,3-pentamethyl-3-vinyldisiloxane | Co$_2$(CNMes)$_8$ | 83 | 30 |
| Example 40 | vinyltriethoxysilane | Co$_2$(CN$^t$Bu)$_8$ | >99 | 53 |

The invention claimed is:
1. A method for producing a product of a hydrosilylation reaction between an aliphatic unsaturated bond-containing compound and a Si—H bond-containing compound, wherein the method comprises contacting the aliphatic unsaturated bond-containing compound and the Si—H bond-containing compound with a catalyst comprising $Co_2(CNtBu)_8$.

2. The method according to claim 1, wherein the aliphatic unsaturated bond-containing compound is an olefin compound, a silane compound or an organopolysiloxane having an alkenyl group bonded to a Si atom.

* * * * *